US010076615B2

(12) United States Patent
Djupesland et al.

(10) Patent No.: US 10,076,615 B2
(45) Date of Patent: Sep. 18, 2018

(54) NASAL DELIVERY

(71) Applicant: OptiNose AS, Oslo (NO)

(72) Inventors: Per Gisle Djupesland, Oslo (NO); Colin David Sheldrake, Wiltshire (GB)

(73) Assignee: OptiNose AS, Oslo (NO)

(*) Notice: Subject to any disclaimer, the term of this patent is extended or adjusted under 35 U.S.C. 154(b) by 479 days.

(21) Appl. No.: 14/618,273

(22) Filed: Feb. 10, 2015

(65) Prior Publication Data

US 2016/0001022 A1 Jan. 7, 2016

Related U.S. Application Data

(63) Continuation of application No. 12/594,361, filed as application No. PCT/GB2008/001217 on Apr. 7, 2008, now Pat. No. 8,978,647.

(30) Foreign Application Priority Data

Apr. 5, 2007 (GB) .................................. 0706863.8

(51) Int. Cl.
*A61M 15/08* (2006.01)
*A61M 15/00* (2006.01)

(52) U.S. Cl.
CPC ...... *A61M 15/085* (2014.02); *A61M 15/0021* (2014.02); *A61M 15/0098* (2014.02);
(Continued)

(58) Field of Classification Search
CPC A61M 11/008; A61M 15/08; A61M 16/0066; A61M 16/0069; A61M 16/0078;
(Continued)

(56) References Cited

U.S. PATENT DOCUMENTS 605,436 A 6/1898 Kellogg
642,748 A 2/1900 Manners
(Continued)

FOREIGN PATENT DOCUMENTS

DE 21 23 252 1/1973
FR 2 854 574 11/2004
(Continued)

OTHER PUBLICATIONS

International Search Report for International App. No. PCT/GB08/01217 (8 pages).
(Continued)

*Primary Examiner* — Annette Dixon
(74) *Attorney, Agent, or Firm* — Finnegan, Henderson, Farabow, Garrett & Dunner, LLP

(57) ABSTRACT

A nasal delivery device for and method of delivering substance to a nasal cavity of a subject, the delivery device comprising: a nosepiece for fitting to a nostril of a subject, wherein the nosepiece comprises a tip element which includes a delivery aperture from which substance is in use delivered into the nasal cavity, and the tip element is at least in part tapered such as to be inclined to a longitudinal axis of the nosepiece, with the delivery aperture extending both laterally across the tip element and along a longitudinal extent of the tip element; a nozzle through which substance is in use delivered, preferably substantially axially to a longitudinal axis of the nosepiece, to the respective nasal cavity; and a delivery unit for delivering substance through the nozzle of the nosepiece.

13 Claims, 28 Drawing Sheets

(52) U.S. Cl.
CPC ....... *A61M 15/08* (2013.01); *A61M 2202/064* (2013.01); *A61M 2210/0625* (2013.01)

(58) Field of Classification Search
CPC ............ A61M 16/009; A61M 16/0093; A61M 16/01; A61M 16/0666; A61M 16/0833; A61M 16/085; A61M 16/101; A61M 16/1015; A61M 16/1055; A61M 16/107; A61M 16/22; A61M 2016/0027; A61M 2016/1025; A61M 2016/103; A61M 2210/0618; A61M 2230/005; A61M 2230/43; A61M 2230/432; A61M 2230/435
USPC ............ 128/200.14, 200.23, 200.26, 203.15, 128/203.22, 204.18, 204.21, 204.23, 128/206.11, 207.14, 207.15, 207.18
See application file for complete search history.

(56) References Cited

U.S. PATENT DOCUMENTS

| | | | |
|---|---|---|---|
| 658,436 A | 9/1900 | Groth | |
| 746,749 A | 12/1903 | Seidel | |
| 794,641 A | 7/1905 | Ramey | |
| 888,869 A | 5/1908 | Clark | |
| 902,832 A | 11/1908 | Philbrook | |
| 2,672,138 A | 3/1954 | Marion | |
| 3,127,893 A | 4/1964 | Montague | |
| 3,198,193 A | 8/1965 | Schwartzman et al. | |
| 4,684,362 A | 8/1987 | Holt | |
| 5,400,797 A * | 3/1995 | Ethridge | A61B 7/003 600/529 |
| 5,788,683 A | 8/1998 | Martin | |
| 5,797,390 A | 8/1998 | McSoley | |
| 5,797,392 A | 8/1998 | Keldmann et al. | |
| 6,561,193 B1 * | 5/2003 | Noble | A61M 16/01 128/207.18 |
| 6,637,434 B2 * | 10/2003 | Noble | A61M 16/01 128/207.18 |
| 6,647,980 B1 | 11/2003 | Gizurarson | |
| 6,648,848 B1 | 11/2003 | Keldmann et al. | |
| 6,701,916 B2 | 3/2004 | Mezzoli | |
| 6,715,485 B1 * | 4/2004 | Djupesland | A61M 3/0279 128/203.12 |
| D530,815 S | 10/2006 | Murphy et al. | |
| 7,178,524 B2 * | 2/2007 | Noble | A61M 16/01 128/206.11 |
| 7,225,807 B2 | 6/2007 | Papania et al. | |
| 7,347,201 B2 | 3/2008 | Djupesland | |
| 7,347,209 B2 | 3/2008 | Bovo | |
| 7,377,901 B2 | 5/2008 | Djupesland et al. | |
| 7,481,218 B2 | 1/2009 | Djupesland | |
| 7,543,581 B2 | 6/2009 | Djupesland | |
| 7,740,014 B2 | 6/2010 | Djupesland | |
| 7,784,460 B2 | 8/2010 | Djupesland et al. | |
| 7,841,337 B2 | 11/2010 | Djupesland | |
| 7,854,227 B2 | 12/2010 | Djupesland | |
| 7,934,503 B2 | 5/2011 | Djupesland et al. | |
| 7,975,690 B2 | 7/2011 | Djupesland | |
| 8,047,202 B2 | 11/2011 | Djupesland | |
| 8,146,589 B2 | 4/2012 | Djupesland | |
| 8,171,929 B2 | 5/2012 | Djupesland et al. | |
| 8,291,906 B2 | 10/2012 | Kooij | |
| 8,327,844 B2 | 12/2012 | Djupesland | |
| 8,511,303 B2 | 8/2013 | Djupesland | |
| 8,522,778 B2 | 9/2013 | Djupesland | |
| 8,550,073 B2 | 10/2013 | Djupesland | |
| 8,555,877 B2 | 10/2013 | Djupesland | |
| 8,555,878 B2 | 10/2013 | Djupesland | |
| 8,590,530 B2 | 11/2013 | Djupesland et al. | |
| 8,596,278 B2 | 12/2013 | Djupesland | |
| 8,800,555 B2 | 8/2014 | Djupesland | |
| 8,875,704 B2 | 11/2014 | Djupesland et al. | |
| 8,899,229 B2 | 12/2014 | Djupesland et al. | |
| 8,910,629 B2 | 12/2014 | Djupesland et al. | |
| D723,156 S | 2/2015 | Djupesland et al. | |
| D725,769 S | 3/2015 | Djupesland et al. | |
| 8,978,647 B2 | 3/2015 | Djupesland et al. | |
| 9,010,325 B2 | 4/2015 | Djupesland et al. | |
| 9,038,630 B2 | 5/2015 | Djupesland et al. | |
| 9,067,034 B2 | 6/2015 | Djupesland et al. | |
| 9,072,857 B2 | 7/2015 | Djupesland | |
| 9,108,015 B2 | 8/2015 | Djupesland | |
| 9,119,932 B2 | 9/2015 | Djupesland | |
| 9,132,249 B2 | 9/2015 | Djupesland | |
| 9,144,652 B2 | 9/2015 | Djupesland et al. | |
| 9,168,341 B2 | 10/2015 | Djupesland | |
| 9,205,208 B2 | 12/2015 | Djupesland | |
| 9,205,209 B2 | 12/2015 | Djupesland | |
| 9,272,104 B2 | 3/2016 | Djupesland | |
| D759,805 S | 6/2016 | Djupesland | |
| D761,951 S | 7/2016 | Djupesland | |
| 9,452,272 B2 | 9/2016 | Djupesland et al. | |
| 9,468,727 B2 | 10/2016 | Djupesland | |
| D773,644 S | 12/2016 | Djupesland | |
| 9,522,243 B2 | 12/2016 | Djupesland | |
| 9,566,402 B2 | 2/2017 | Djupesland | |
| 9,649,456 B2 | 5/2017 | Djupesland et al. | |
| 2003/0079742 A1 | 5/2003 | Giroux | |
| 2003/0101992 A1 | 6/2003 | Mezzoli | |
| 2003/0133877 A1 | 7/2003 | Levin | |
| 2004/0024330 A1 | 2/2004 | Djupesland et al. | |
| 2004/0112378 A1 | 6/2004 | Djupesland | |
| 2004/0112379 A1 | 6/2004 | Djupesland | |
| 2004/0112380 A1 | 6/2004 | Djupesland | |
| 2004/0134494 A1 | 7/2004 | Papania et al. | |
| 2004/0149289 A1 | 8/2004 | Djupesland | |
| 2004/0182388 A1 | 9/2004 | Djupesland | |
| 2005/0028812 A1 | 2/2005 | Djupesland | |
| 2005/0072430 A1 | 4/2005 | Djupesland | |
| 2005/0235992 A1 | 10/2005 | Djupesland | |
| 2005/0287107 A1 | 12/2005 | Tuccelli | |
| 2006/0096589 A1 | 5/2006 | Djupesland | |
| 2006/0107957 A1 | 5/2006 | Djupesland | |
| 2006/0135975 A1 | 6/2006 | Perkins | |
| 2006/0169278 A1 | 8/2006 | Djupesland et al. | |
| 2006/0169285 A1 | 8/2006 | Bovo | |
| 2006/0174889 A1 | 8/2006 | Noble | |
| 2006/0219240 A1 | 10/2006 | Djupesland | |
| 2006/0219241 A1 | 10/2006 | Djupesland | |
| 2006/0225732 A1 | 10/2006 | Djupesland | |
| 2006/0231094 A1 | 10/2006 | Djupesland | |
| 2007/0039614 A1 | 2/2007 | Djupesland | |
| 2007/0062538 A1 * | 3/2007 | Foggia | A61M 15/085 128/207.18 |
| 2007/0125371 A1 | 6/2007 | Djupesland | |
| 2007/0186927 A1 | 8/2007 | Djupesland et al. | |
| 2008/0161771 A1 | 7/2008 | Djupesland | |
| 2008/0163874 A1 | 7/2008 | Djupesland | |
| 2008/0221471 A1 | 9/2008 | Djupesland et al. | |
| 2008/0223363 A1 | 9/2008 | Djupesland | |
| 2008/0276938 A1 * | 11/2008 | Jeppesen | A61M 16/0666 128/204.18 |
| 2008/0289629 A1 | 11/2008 | Djupesland et al. | |
| 2009/0101146 A1 | 4/2009 | Djupesland | |
| 2009/0293873 A1 | 12/2009 | Djupesland et al. | |
| 2009/0304802 A1 | 12/2009 | Djupesland et al. | |
| 2009/0314293 A1 | 12/2009 | Djupesland | |
| 2009/0320832 A1 | 12/2009 | Djupesland | |
| 2010/0000534 A1 | 1/2010 | Kooij et al. | |
| 2010/0035805 A1 | 2/2010 | Hafner | |
| 2010/0051022 A1 | 3/2010 | Djupesland et al. | |
| 2010/0057047 A1 | 3/2010 | Djupesland et al. | |
| 2010/0242959 A1 | 9/2010 | Djupesland et al. | |
| 2010/0282246 A1 | 11/2010 | Djupesland et al. | |
| 2010/0288275 A1 | 11/2010 | Djupesland et al. | |
| 2010/0300439 A1 | 12/2010 | Djupesland et al. | |
| 2011/0023869 A1 | 2/2011 | Djupesland | |
| 2011/0053827 A1 | 3/2011 | Hafner | |
| 2011/0088690 A1 | 4/2011 | Djupesland et al. | |
| 2011/0088691 A1 | 4/2011 | Djupesland | |
| 2011/0114087 A1 | 5/2011 | Djupesland et al. | |
| 2011/0126830 A1 | 6/2011 | Djupesland et al. | |

(56) References Cited

U.S. PATENT DOCUMENTS

| | | | |
|---|---|---|---|
| 2011/0259329 A1 | 10/2011 | Djupesland et al. |
| 2011/0318345 A1 | 12/2011 | Djupesland |
| 2012/0000459 A1 | 1/2012 | Djupesland |
| 2012/0006323 A1 | 1/2012 | Djupesland |
| 2012/0073571 A1 | 3/2012 | Djupesland |
| 2012/0090608 A1 | 4/2012 | Djupesland et al. |
| 2012/0260915 A1 | 10/2012 | Djupesland |
| 2013/0098362 A1 | 4/2013 | Djupesland et al. |
| 2013/0125889 A1 | 5/2013 | Djupesland et al. |
| 2013/0327320 A1 | 12/2013 | Djupesland |
| 2014/0018295 A1 | 1/2014 | Djupesland |
| 2014/0041660 A1 | 2/2014 | Djupesland et al. |
| 2014/0060536 A1 | 3/2014 | Djupesland |
| 2014/0073562 A1 | 3/2014 | Djupesland |
| 2014/0144442 A1 | 5/2014 | Djupesland et al. |
| 2014/0144443 A1 | 5/2014 | Djupesland et al. |
| 2014/0166008 A1 | 6/2014 | Djupesland |
| 2014/0202456 A1 | 7/2014 | Djupesland |
| 2014/0246022 A1 | 9/2014 | Djupesland et al. |
| 2015/0007811 A1 | 1/2015 | Djupesland et al. |
| 2015/0013670 A1 | 1/2015 | Djupesland et al. |
| 2015/0013677 A1 | 1/2015 | Djupesland et al. |
| 2015/0053201 A1 | 2/2015 | Djupesland et al. |
| 2015/0090259 A1 | 4/2015 | Djupesland et al. |
| 2015/0101605 A1 | 4/2015 | Djupesland et al. |
| 2015/0144129 A1 | 5/2015 | Djupesland et al. |
| 2015/0165139 A1 | 6/2015 | Hafner |
| 2015/0182709 A1 | 7/2015 | Djupesland |
| 2015/0246194 A1 | 9/2015 | Djupesland et al. |
| 2015/0367090 A1 | 12/2015 | Djupesland et al. |
| 2015/0367091 A1 | 12/2015 | Djupesland et al. |
| 2016/0001022 A1 | 1/2016 | Djupesland et al. |
| 2016/0045687 A1 | 2/2016 | Djupesland |
| 2016/0051778 A1 | 2/2016 | Djupesland et al. |
| 2016/0074603 A1 | 3/2016 | Djupesland et al. |
| 2016/0082206 A1 | 3/2016 | Djupesland et al. |
| 2016/0082207 A1 | 3/2016 | Djupesland et al. |
| 2016/0095993 A1 | 4/2016 | Djupesland |
| 2016/0166788 A1 | 6/2016 | Djupesland et al. |
| 2016/0184537 A1 | 6/2016 | Djupesland |
| 2016/0193435 A1 | 7/2016 | Djupesland |
| 2016/0250408 A1 | 9/2016 | Djupesland |
| 2016/0263334 A1 | 9/2016 | Djupesland |
| 2016/0279357 A1 | 9/2016 | Djupesland |
| 2016/0310683 A1 | 10/2016 | Djupesland et al. |
| 2016/0331916 A1 | 11/2016 | Djupesland et al. |
| 2016/0367771 A1 | 12/2016 | Djupesland |
| 2016/0367772 A1 | 12/2016 | Djupesland |
| 2016/0367774 A1 | 12/2016 | Djupesland et al. |
| 2017/0043108 A1 | 2/2017 | Djupesland et al. |
| 2017/0151397 A1 | 6/2017 | Djupesland |
| 2017/0203061 A1 | 7/2017 | Djupesland et al. |

FOREIGN PATENT DOCUMENTS

| | | |
|---|---|---|
| GB | 2418147 | 3/2006 |
| GB | 2435835 | 9/2007 |
| JP | 09/135901 | 5/1997 |
| WO | WO 94/17753 | 8/1994 |
| WO | WO 96/22802 | 8/1996 |
| WO | WO 98/53869 | 12/1998 |
| WO | WO 99/49923 | 10/1999 |
| WO | WO 00/51672 | 9/2000 |
| WO | WO 01/97689 | 12/2001 |
| WO | WO 02/068029 | 9/2002 |
| WO | WO 02/068030 | 9/2002 |
| WO | WO 02/068031 | 9/2002 |
| WO | WO 02/068032 | 9/2002 |
| WO | WO 03/000310 | 1/2003 |
| WO | WO 03/020350 | 3/2003 |
| WO | WO 03/082393 | 10/2003 |
| WO | WO 03/084591 | 10/2003 |
| WO | WO 03/090812 | 11/2003 |
| WO | WO 2004/004814 | 1/2004 |
| WO | WO 2004/004922 | 1/2004 |
| WO | WO 2004/060433 | 7/2004 |
| WO | WO 2004/103447 | 12/2004 |
| WO | WO 2005/016423 | 2/2005 |
| WO | WO 2005/021059 | 3/2005 |
| WO | WO 2006/030210 | 3/2006 |
| WO | WO 2006/090149 | 8/2006 |
| WO | WO 2007/083073 | 7/2007 |
| WO | WO 2007/093784 | 8/2007 |
| WO | WO 2007/093791 | 8/2007 |
| WO | WO 07/102089 | 9/2007 |
| WO | WO 2007/099361 | 9/2007 |
| WO | WO 2007/102089 | 9/2007 |
| WO | WO 2007/107887 | 9/2007 |
| WO | WO 2007/125318 | 11/2007 |
| WO | WO 2007/141541 | 12/2007 |
| WO | WO 2008/012531 | 1/2008 |
| WO | WO 2008/065403 | 6/2008 |
| WO | WO 2008/081326 | 7/2008 |
| WO | WO 2008/081327 | 7/2008 |
| WO | WO 2008/122791 | 10/2008 |
| WO | WO 2008/122795 | 10/2008 |
| WO | WO 2009/044172 | 4/2009 |
| WO | WO 2010/029441 | 3/2010 |
| WO | WO 2012/035427 | 3/2012 |
| WO | WO 2012/123819 | 9/2012 |
| WO | WO 2013/124491 | 8/2013 |
| WO | WO 2013/124492 | 8/2013 |
| WO | WO 2013/124493 | 8/2013 |
| WO | WO 2014/155192 | 10/2014 |

OTHER PUBLICATIONS

International Preliminary Report on Patentability App. No. PCT/GB08/01217 (12 pages).
"Longitudinal." Collins English Dictionary. 2000. http://www.credoreference.com/entry/hcengdict/longitudinal (Dec. 14, 2013).
Abstract for FR2854574, espacenet.
Abstract for DE 21 23 252, Thompson Innovation.
Cindy H. Dubin, *Nothing to Sneeze At*, Pharmaceutical Formulation & Quality Magazine (Jan. 29, 2003).
Per Gisle Djupesland, *Nasal Delivery of Vaccines*, EPC (Jan. 29, 2003).
Per Gisle Djupesland, *Who Nose How Far Nasal Delivery Can Go?*, EPC (Oct. 7, 2003).
Per Gisle Djupesland, *Bi-directional Nasal Drug Delivery*, Innovations in Pharmaceutical Technology (Jul. 10, 2004).
P.G. Djupesland, *Bi-Directional Nasal Delivery of Aerosols Can Prevent Lung Deposition*, Journal of Aerosol Medicine (Sep. 2004).
*Bi-Directional Nasal Device Delivers Drug on Exhalation*, Pharmaceutical Technology (Sep. 10, 2004).
Ola Dale et al., *Intranasal Midazolam: A Comparison of Two Delivery Devices in Human Volunteers*, Journal of Pharmacy and Pharmacology (Oct. 2004).
G. Furness, *Nasal Drug Delivery: Rapid Onset Via a Convenient Route*, ONdrugDelivery Ltd. (2005).
M. Kleven, *Using Computational Fluid Dynamics (CFD) to Improve the Bi-Directional Nasal Drug Delivery Concept*, Trans IChemE Part C. (Jun. 2005).
Per Gisle Djupesland, *Breath-Actuated Bi-Directional Delivery Sets the Nasal Market on a New Course*, ONdrugDelivery (Oct. 10, 2005).
Hilde Bakke et al., *Oral Spray Immunization May be an Alternative to Intranasal Vaccine Delivery to Induce Systemic Antibodies But Not Nasal Mucosal or Cellular Immunity*, Scan J. of Immunol. (Mar. 2006).
P.G. Djupesland et al., *Breath Actuated Nasal Device Improves Delivery to Target Sites Beyond the Nasal Valve*, The Laryngoscope (Mar. 2006).
R. Luthringer et al., *Rapid Absorption of Sumatriptan Powder and Effects on Glyceryl tinitrate Model of Headache Following Intranasal Delivery Using a Novel Bi-Directional Device*, Journal of Pharmacy and Pharmacology (Jan. 2009).
A. Skretting et al., *A New Method for Scintigraphic Quantification of Deposition and Clearance in Anatomical Regions of the Human Nose*, Nuclear Medicine Communications (Aug. 2009).

(56) References Cited

OTHER PUBLICATIONS

Vlckovia et al., *Effective Treatment of Mild-to-Moderate Nasal Polyposis with Fluticasone Delivered by a Novel Device*, Rhinology (Oct. 22, 2009).

Per Gisle Djupesland et al., *Impact of Baseline Nasal Polyp Size and Previous Surgery on Efficacy of Fluticasone Delivered With a Novel Device: A Subgroup Analysis*, Am. J. Rhinology Allergy (2010).

P.G. Djupesland et al., *Intranasal Sumatriptan Powder Delivered by a Novel Breath Actuated Bi-Directional Device for the Acute Treatment of Migraine: A Randomised Placebo-Controlled Study*, Cephalalgia (Mar. 17, 2010).

F.S. Hansen et al., *Preliminary Efficacy of Fluticasone Delivered by a Novel Device in Recalcitrant Chronic Rhinosinusitis*, Rhinology (Jun. 26, 2010).

Per Gisle Djupesland, *Nasal Drug Delivery Devices: Characteristics and Performance in Clinical Perspective—A Review*, Drug. Deliv. and Transl. Res. (Oct. 18, 2012).

Per Gisle Djupesland, *Nasal Deposition and Clearance in Man: Comparison of a Bidirectional Powder Device and a Traditional Liquid Spray Pump*, Journal of Aerosol Medicine and Pulmonary Drug Delivery (Nov. 2012).

Stewart J. Tepper, *Clinical Implications for Breath-Powered Powder Sumatriptan Intranasal Treatment*, Headache, The American Headache Society (Apr. 29, 2013).

Mohammad Obaidi et al., *Improved Pharmacokinetics of Sumatriptan With Breath Powered Nasal Delivery of Sumatriptan Powder*, Headache, The American Headache Society (May 24, 2013).

Per Gisle Djupesland, *Breath Powdered Nasal Delivery: A New Route to Rapid Headache Relief*, Headache, The American Headache Society (Jun. 4, 2013).

Per Gisle Djupesland et al., *The Nasal Approach to Delivering Treatment for Brain Diseases: An Anatomic, Physiologic, and Delivery Technology Overview*, Therapeutic Delivery (2014).

R.K. Cady et al., *A Randomized Double-Blind, Placebo Controlled Study of Breath Powered Nasal Delivery of Sumatriptan Powder (AVP-825) in the Treatment of Acute Migraine (The Target Study)*, Headache (Sep. 8, 2014).

S.J. Tepper et al., *AVP-825 Breath-Powdered Intranasal Delivery System Containing 22 mg Sumatriptan Powder vs. 100 mg Oral Sumatripta in the Acute Treatment of Migraines (The Compass Study): A Comparative Randomized Clinical Trial Across Multiple Attacks*, Headache: The Journal of Head and Face Pain (Mar. 29, 2015).

D. S. Quintana et al., *Low-dose Oxytocin Delivered Intranasally with Breath Powdered Device Affects Social-Cognitive Behavior: A Randomized Four-Way Crossover Trial with Nasal Cavity Dimension Assessment*, Transl Psychiatry (Jul. 14, 2015).

R. Mahmoud, *Breathe Out*, Innovations in Phar, Tech. (Dec. 10, 2015).

\* cited by examiner

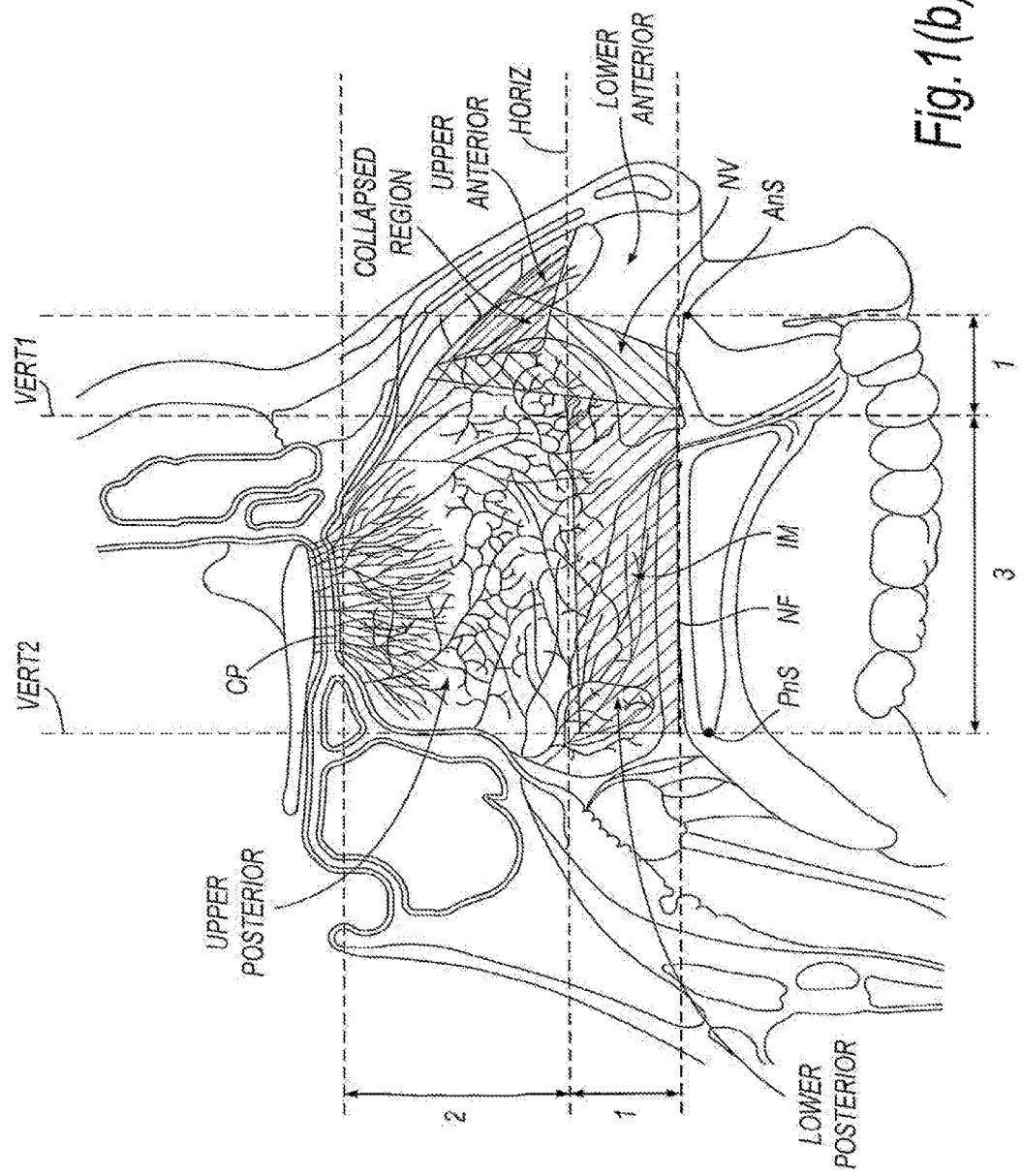

NASAL DELIVERY

This is a continuation application of U.S. application Ser. No. 12/594,361, filed Jul. 16, 2010, which is the national stage entry of PCT/GB2008/001217, which claims priority to GB 0706863.8, filed Apr. 5, 2007 each of which are incorporated herein by reference.

The present invention relates to a nasal delivery device for and a method of delivering a substance, in particular one of a liquid, as a suspension or solution, or a powder containing a medicament, especially systemic or topical pharmaceuticals, or a vaccine to the nasal airway of a subject.

Referring to FIG. 1(a), the nasal airway 1 comprises the two nasal cavities separated by the nasal septum, which airway 1 includes numerous ostia, such as the paranasal sinus ostia 3 and the tubal ostia 5, and olfactory cells, and is lined by the nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved on exhalation through the oral cavity 9, and in dashed line in the open position.

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion. Medicaments that are commonly topically delivered include decongestants, anti-histamines, cromoglycates, steroids and antibiotics. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Medicaments can also be systemically delivered through the nasal pathway, the nasal pathway offering a good administration route for the systemic delivery of pharmaceuticals, such as hormones, for example, oxytocin and calcitonin, and analgetics, such as anti-migraine compositions, as the high blood flow and large surface area of the nasal mucosa advantageously provides for rapid systemic uptake.

Nasal delivery is also expected to be advantageous for the administration of medicaments requiring a rapid onset of action, for example, analgetics, anti-emetics, insulin, anti-epileptics, sedatives and hypnotica, and also other pharmaceuticals, for example, cardio-vascular drugs. It is envisaged that nasal administration will provide for a fast onset of action, at a rate similar to that of injection and at a rate much faster than that of oral administration. Indeed, for the treatment of many acute conditions, nasal administration is advantageous over oral administration, since gastric stasis can further slow the onset of action following oral administration.

It is also expected that nasal delivery could provide an effective delivery route for the administration of proteins and peptides as produced by modern biotechnological techniques. For such substances, the metabolism in the intestines and the first-pass-effect in the liver represent significant obstacles for reliable and cost-efficient delivery.

Furthermore, it is expected that nasal delivery using the nasal delivery technique of the present invention will prove effective in the treatment of many common neurological diseases, such as Alzheimer's, Parkinson's, psychiatric diseases and intracerebral infections, where not possible using existing techniques. The nasal delivery technique of the present invention allows for delivery to the olfactory region, which region is located in the superior region of the nasal cavities and represents the only region where it is possible to circumvent the blood-to-brain barrier (BBB) and enable communication with the cerebrospinal fluid (CSF) and the brain.

Also, it is expected that the nasal delivery technique of the present invention will allow for the effective delivery of vaccines.

Aside from the delivery of medicaments, the irrigation of the nasal mucosa with liquids, in particular saline solutions, is commonly practised to remove particles and secretions, as well as to improve the mucociliary activity of the nasal mucosa. These solutions can be used in combination with active pharmaceuticals.

For any kind of drug delivery, accurate and reliable dosing is essential, but it is of particular importance in relation to the administration of potent drugs which have a narrow therapeutic window, drugs with potentially serious adverse effects and drugs for the treatment of serious and life-threatening conditions. For some conditions, it is essential to individualize the dosage to the particular situation, for example, in the case of diabetes mellitus. For diabetes, and, indeed, for many other conditions, the dosage of the pharmaceutical is preferably based on actual real-time measurements. Currently, blood samples are most frequently used, but the analysis of molecules in the exhalation breath of subjects has been proposed as an alternative to blood analysis for several conditions. Breath analysis is currently used for the diagnosis of conditions such as *helicobacter pylori* infections which cause gastric ulcers.

WO-A-00/51672 discloses a delivery device for delivering a substance, in particular a medicament, in a bi-directional flow through the nasal cavities, that is, an air flow which passes into one nostril, around the posterior margin of the nasal septum and in the opposite direction out of the other nostril. This bi-directional air flow advantageously acts to stimulate the sensory nerves in the nasal mucosa, thereby conditioning the subject for the delivery and providing a more comfortable delivery situation.

It is an aim of the present invention to provide improved nasal delivery devices and nasal delivery methods for providing for the improved delivery of substance to a nasal cavity of subject.

One particular aim of the present invention is to optimize the shape, direction and particle distribution of the plume of a delivered dose, in order to reach targeted regions and reduce deposition outside these regions.

Another particular aim of the present invention is to provide for improved targeting of specific regions of the nasal airway and improved reproducibility and consistency of dosing.

The present inventors have recognized that an increased delivery of substance to the posterior region of the nasal airway, and in particular the upper posterior region of the nasal airway, as illustrated in FIG. 1(b), relative to the anterior region of the nasal airway, surprisingly provides for a disproportionately greater effect, in particular a CNS effect, which is suggestive of a greater uptake of substance into the CNS than would be predicted from the blood plasma concentration of the substance, but also systemic absorption and local action.

The posterior region of the nasal airway is that region which is posterior of the nasal valve NV, as illustrated in FIG. 1(*b*).

The nasal valve NV comprises the anterior bony cavum which contains inferior turbinate erectile tissue and septal erectile tissue, which are supported respectively by compliant ala tissue and the rigid cartilaginous septum (Cole). These elements combine to form a dynamic valve, which extends over several millimeters, that adjusts nasal airflow, and is stabilized by cartilage and bone, modulated by voluntary muscle and regulated by erectile tissue. The lumen of the nasal valve NV is the section of narrowest cross-sectional area between the posterior and anterior regions of the nasal airway, and is much longer and narrower dorsally than ventrally, and this lumen defines a triangular entrance which extends to the piriform region of the bony cavum. The nasal valve NV is lined in its anterior part with transitional epithelium, with a gradual transition posterior to respiratory epithelium. The nasal valve NV and anterior vestibule define roughly the anterior one-third of the nose.

In human subjects, the upper lateral wall of the nasal valve NV collapses to form a collapsed region, as illustrated in FIG. 1(*b*), which significantly narrows the upper part of the nasal valve NV and obstructs access to the upper posterior region of the nasal cavity, and in particular the olfactory region. This collapsed region, in combination with the upper lateral wall of the nasal valve NV having a curved shape, makes the insertion of a rigid structure into the lumen of the nasal valve NV particularly difficult and uncomfortable. This discomfort is in part caused by the very sensitive lining at the nasal valve NV, and the act of insertion is also liable to cause sneezing which is induced by a "tickling" effect, which can be diminished by configuring the nosepiece to have a flexible structure which provides for a firm, continuous contact.

The posterior region of the nasal airway is that region which is lined with respiratory epithelium, which is ciliated, and olfactory epithelium, which comprises nerves which extend downwards through the cribiform plate CP from the olfactory bulb, whereas the anterior region of the nasal airway is that region which is lined with squamous epithelium, which is not ciliated, and transitional epithelium which has no or few cilia. The olfactory epithelium extends on both the lateral and medial sides of the nasal airway, and typically extends downwards about 1.5 to 2.5 cm.

The upper posterior region is the region above the inferior meatus IM, as illustrated in FIG. 1(*b*), and encompasses the middle turbinate, the sinus ostia in infundibulum (ostia to maxillary, frontal and ethmoidal sinuses), the olfactory region, and the upper branches of the trigeminal nerve, and is that region which includes veins which drain to the venous sinuses that surround the brain.

As illustrated in FIG. 1(*b*), the posterior region of the nasal airway is the nasal region posterior of an imaginary vertical plane VERT1 which is located at a position corresponding to one-quarter of the distance between the anterior nasal spine AnS, which is a pointed projection at the anterior extremity of the intermaxillary suture, and the posterior nasal spine PnS, which is the sharp posterior extremity of the nasal crest of the hard palate and represents the transition between the nose and the nasopharynx, which corresponds to a distance posterior of the anterior nasal spine AnS of between about 13 mm and about 14 mm (Rosenberger defines the distance between the anterior nasal spine AnS and the posterior nasal spine PnS as being 56 mm in eighteen year old boys and 53.3 mm in eighteen year old girls). As again illustrated in FIG. 1(*b*), the posterior nasal region is bounded posteriorly by an imaginary vertical plane VERT2 which extends through the posterior nasal spine PnS.

As further illustrated in FIG. 1(*b*), the upper region of the nasal airway is an upper segment of the nasal airway which is bounded by the cribiform plate CP and a horizontal plane HORIZ which is located at a position corresponding to one-third of the distance between the nasal floor NF of the nasal airway and the cribiform plate CP, which corresponds to a height of typically between about 13 and about 19 mm above the nasal floor NF (Zacharek et al define the distance from the nasal floor NF to the cribiform plate CP as 46+/−4 mm).

The upper posterior region is thus that upper posterior region which is bounded by the above-defined vertical and horizontal planes VERT1, HORIZ.

The present inventors have postulated that this increased concentration within the CNS arises as a result of the veins in the upper posterior region of the nasal airway draining backwards to the venous sinuses that surround the brain, which leads to a higher local concentration in the cerebrovasculature. Although the sinus cavernous is outside the blood-to-brain barrier, animal models have shown that substances can be transported by a counter-current mechanism from the veins therein to the carotid artery which passes through the sinus cavernous. Other mechanisms have been proposed which include extra axonal transport along the surface of the olfactory and trigeminal nerves. This mode of transport is apparently quite rapid as compared to intra axonal transport.

The improved efficacy as achieved by the present invention as compared to existing nasal spray administration systems can apparently be explained in that such nasal spray administration systems have been determined initially to deliver largely to the anterior one-third of the nasal airway, that is, the nasal region anterior of the nasal valve, from which region drainage is mainly along the floor of the nose and in which region the veins drain to the external facial vein, which in turn drains to the external carotid and in turn to the peripheral circulation.

In one aspect the present invention provides a nasal delivery device for delivering substance to a nasal cavity of a subject, the delivery device comprising: a nosepiece for fitting to a nostril of a subject, wherein the nosepiece comprises a tip element which includes a delivery aperture from which substance is in use delivered into the nasal cavity, and the tip element is at least in part tapered such as to be inclined to a longitudinal axis of the nosepiece, with the delivery aperture extending both laterally across the tip element and along a longitudinal extent of the tip element; a nozzle through which substance is in use delivered, preferably substantially axially to a longitudinal axis of the nosepiece, to the respective nasal cavity; and a delivery unit (also referred to as a substance supply unit) for delivering substance through the nozzle of the nosepiece.

In another aspect the present invention provides a nosepiece for delivering substance to a nasal cavity of a subject, the nosepiece comprising a tip element which includes a delivery aperture from which substance is in use delivered into the nasal cavity, preferably substantially axially to a longitudinal axis of the nosepiece, and the tip element is at least in part tapered such as to be inclined to a longitudinal axis of the nosepiece, with the delivery aperture extending both laterally across the tip element and along a longitudinal extent of the tip element.

In a further aspect the present invention provides a nasal delivery device for delivering substance to a nasal cavity of a subject, the delivery device comprising: a housing; a nosepiece for fitting to a nostril of a subject, through which substance is in use delivered into the nasal cavity; a delivery unit for delivering substance through the nosepiece; and a nose gripping member which receives a finger of the subject and is configured such as to be brought into contact with the skin of the nare of the nostril into which the nosepiece is inserted, such as to allow the skin of the nare of the nostril to be drawn over the nosepiece and promote fitting of the nosepiece in the nasal cavity of the subject.

In a yet further aspect the present invention provides a method of fitting a nasal delivery device to a nostril of a subject, the method comprising the steps of: providing a nasal delivery device which comprises a nosepiece through which substance is delivered to a nasal cavity of the subject; inserting the nosepiece into one of the nostrils of the subject; twisting the nosepiece in the nostril, such as to align the delivery device; pressing a finger against the skin of the nose, such as to press the nare of the nostril against the nosepiece; and retracting the finger, such as to pull the nare of the nostril over the nosepiece.

In one embodiment the present invention provides a nosepiece which provides for expansion in the sagittal plane, opening the connection of the mucosal surfaces of the nasal valve and isthmus, in particular by expansion of the collapsed region at the upper lateral wall of the nasal valve.

In another embodiment the present invention provides a nosepiece which includes a flexible tip to fit the cross-sectional shape of a nasal cavity. In a preferred embodiment the nosepiece has an internal configuration, at least at the tip, which acts to prevent collapse and maintain a stable cross-sectional area and a relatively-stable resistance.

In a further embodiment the present invention provides a spray nozzle which provides an asymmetrical spray plume, where either a powder or a liquid.

The present invention is particularly advantageous when used in combination with bi-directional nasal delivery, but is not restricted to such delivery.

The present invention can be combined with delivery concepts which generate a mist, an aerosol, an aerosol spray of particles, either liquid or powder, drops, droplets, or liquid jet of liquid.

An entraining flow can be provided by the exhalation breath of the subject or from an external flow source, such as from an air chamber or a compressed air supply.

The delivery device can be triggered, such that one or both of the dose and gas flow are triggered by an intraoral pressure which is such as to close the oropharyngeal velum or by another event, which may or may not secure velum closure.

The present invention also finds application in delivery systems which do not utilize an auxiliary gas flow and even with inhalation environments which provide for nasal inhalation or a sniffing manoeuvre through one or both of the nostrils.

The devices can be a multi-dose or single-dose.

Preliminary results in models and gamma-scintigraphic pilot studies show that it is possible to improve the access to and deposition in the narrow passages of the upper region of the nasal airway including the olfactory region, the regions with veins draining to the sinus cavernous and innervated by the trigeminal nerve.

Furthermore, experiments in models and humans show that modification of the plume geometry and/or positioning of the nozzle provides for optimal delivery.

U.S. Pat. No. 6,647,980 discloses a device which utilizes a modified plume in order to attempt to decrease lateral deposition, and thereby increase the amount of the dose which reaches the upper region of the nasal airway. Although this device may provide for reduced deposition in the anterior part of the nasal cavity which is lined by squamous epithelium, owing to the narrower cone angle, only a moderate increase in deposition in the upper region of the nose is expected to be achieved, owing to the difficult and protected access to this region. Furthermore, narrowing of the nose during inhalation, as caused by the Bernoulli effect, will further narrow the nasal cavity to increase the fraction deposited in valve region.

In its preferred embodiment the present invention provides for a bi-directional air flow in the nasal passages in which optimally-sized particles are entrained and subsequently delivered to appropriate target sites in the nasal airway.

The present invention aims further to improve upon the devices as disclosed in the applicant's earlier WO-A-03/000310, the content of which is herein incorporated by reference.

In one embodiment the present invention provides for optimisation of the delivery to upper parts of the nasal airway, including the olfactory region, by configuring the nosepiece, in particular the shape and position thereof, and the emitted plume of particles or liquid jet in conjunction.

The present invention provides for significantly enhanced access and deposition in the upper region of the nasal airway, and thereby improved dose-to-dose consistency and repeatability of drug delivery to this region of the nasal airway.

The delivery device of the present invention provides both for positioning of the outlet nozzle and the expansion of the upper lateral and medial surfaces of the valve region of a nasal cavity.

By configuring the external and internal shape of the nosepiece, the nosepiece both ensures the correct positioning of the outlet nozzle and optimizes the vertical expansion of the nasal cavity.

The operative function of the nosepiece of the present invention, in vertically expanding the nasal cavity, can be contrasted to that of a conventional, frusto-conical nosepiece, which, during insertion into a nasal cavity, has been found by the present inventor to push the soft, nasal tissue rearwardly, which is particularly disadvantageous where attempting delivery to posterior regions of the nasal airway.

In its preferred embodiment the present invention provides a narrow nosepiece which can be easily slid into a nasal cavity beyond the nasal valve to the required depth, before expansion in the vertical or sagittal plane.

This expanding movement of the nosepiece can either be to the upper part, the lower part or both the upper and lower parts.

In one embodiment the nosepiece comprises two members, that is, an upper and a lower member, where on one both of the members is movable relative to the supporting body. Such members are exemplified by a pair of scissors, a pair of pliers and expansion screws.

In another embodiment the nosepiece could comprise an expanding cuff-like member, which comprises one or both of upper and lower cuff members which expands in the vertical plane.

In one embodiment the nosepiece can comprise a moderately-flexible anterior part such as to allow the nosepiece to adapt to the curved shape of a nasal passage, and thereby facilitate deeper insertion into the nasal slit, and even into the bony part thereof.

In a preferred embodiment the nosepiece includes internal features, such as ribs, which prevent collapse of the flow path and prevents substantial reduction in the internal cross-sectional area, which would otherwise lead to an increase in flow resistance.

This flexibility enables the nosepiece to conform, at least in part, to the different shapes and directions of the nasal passage in this region, but at the same time assists in expanding the isthmus. Though the shape of the anterior part of the nasal passage normally varies within a pre-defined range, pathological deviations may cause more pronounced changes which otherwise may create problems for insertion and positioning of the nosepiece, and hence efficient delivery.

Furthermore, this adaptation of the anterior shape of the nosepiece to conform to the nasal passage provides for reduced turbulence, which would otherwise lead to unwanted deposition in the zone of turbulence.

The present invention also provides for a nozzle, such as the swirl chamber of a spray pump or a pMDI or a nebulizer, which delivers a modified, asymmetric plume of particles.

In its preferred embodiment the plume is an asymmetric plume which is relatively flat, with a small dimension in one axis and much greater in the other axis.

Such a shaped plume reduces deposition in the anterior part of the valve region and increases the fraction of the dose entering into the upper, more posterior region of the nasal passage including the olfactory region and the sinus ostia, which is located below the middle meatus.

The present invention also extends to means for securing a correct and reproducible positioning of nosepiece.

Positioning of the delivery device can be achieved by the function of the mouthpiece or an exit resistor in the exit nostril of a bi-directional device, or as a separate feature with the main function of assisting positioning of the nosepiece. Triangular-shaped nose pieces assist in achieving the correct positioning. The mouthpiece of a device intended for bi-directional delivery also assists in achieving a reproducible positioning of the nosepiece. The provision of a nosepiece in the contralateral nostril also assists in achieving a reproducible positioning of the nosepiece. The provision of a special cap or the like as applied to the exterior of the exterior nose also assists in achieving a reproducible positioning of the nosepiece. Also, tape or vacuum can be used to assist in positioning of the nose piece and potentially in addition helps expanding the valve region by external action, such as an external dilator used to open the nose ("Breath-Right" nasal strip).

The present invention extends to devices which are adapted to bi-directional delivery where driven by the exhalation breath of the subject or an auxiliary gas source, and conventional nasal delivery devices which do not utilize an auxiliary gas flow.

Furthermore, the present invention can be adapted to any traditional delivery modality, including but not restricted to a spray pump, a pMDI, a nebulizer or any other means of delivering liquid jets, particles or drops, either in powder or liquid form, and is not restricted to bi-directional devices.

In its preferred embodiment the present invention provides for expansion in the vertical or sagittal plane, but the expansion is not restricted to this plane. The expansion can be a combination of movement in different planes.

The expansion can be only or predominantly to the upper part or the lower part of a nasal cavity, or the upper and lower parts in combination.

The expansion can be achieved by any possible movement, such as pushing, pulling, lifting, pressing, rotating, expanding, flexing, suction (vacuum) and even by secondary chemical reactions initiated by, for example, pressure, moisture and temperature which create the desired movement of retraction of a mass or volume.

In one embodiment, where the nosepiece comprises two movable members in the form of a speculum, one of the members can provide a delivery channel through which substance is delivered into the nasal airway, and the other member can include a pressure-sensitive release valve or an open channel which allows for the venting of particles from the nasal airway. Such a configuration has particular application in relation to a completely obstructed nose, where the delivered flow would otherwise have no means of escape.

Where the substance includes relatively-large particles, those particles will due to their momentum travel forward and deposit on an opposing surface, whereas the air flow will deviate and flow towards the exit valve.

In having an on/off valve which opens at a predetermined pressure which is just above the pressure where bi-directional flow is expected to occur in a moderately-blocked nose, an air flow will occur suddenly and carry the particles forward, and this will entrain the particles or at least a large fraction of the particles into the blocked nose and onto an opposing surface before the airflow turns around and exits in the opposite direction through the valve.

The valve can have a filter to prevent the particles from escaping to the atmosphere. Using large particles, such as from about 100 µm to about 200 µm, will also avoid or at least reduce this problem.

By providing a relatively-large distance between the point of emission, which is preferably in the upper member, and the point of exit, which is preferably in the lower arm, will increase deposition.

In a preferred embodiment the positioning of the nosepiece should preferably occur prior to release of substance, but could also occur in sequence immediately prior to or simultaneously with the releasing action.

The preferred action is as follows. The positioning and expansion of the specialized nozzle can be achieved by a finger action. When complete, this action will also open the flow path permitting delivery of substance into the nasal airway, preferably by bi-directional delivery, but alternatively also even in the absence of bi-directional delivery. Alternatively, a pre-charged spring or similar can be released when the nosepiece is inserted into a nostril to the correct position. When this positioning action is complete, a valve is opened, making it possible to blow through the device or alternatively release the force from a gas chamber or another stored force, or alternatively allowing a mechanical action by hand compression, similar to actuation of a spray pump. In an alternative configuration, which can be utilized with or without bi-directional flow, for example, when used in infants and unconscious subjects, the two actions of expansion and release of substance from, for example, a spray pump can be integrated. The first part of the mechanical action/compression of a lever by the finger will secure the expansion of the lever and positioning of the nosepiece. Then, when a certain trigger point or resistance is reached the finger force will result in the generation of a spray or release of a compressed gas by exhalation against a resistor or from a pressurized compartment or the combination thereof.

The following represent potential areas of application. Delivery to the olfactory epithelium for transport into or along nerve paths or by diffusion across the cribiform plate. Delivery to the upper part of the nasal passage including the olfactory region which drains via veins to the sinus cavernous to achieve higher concentrations of drugs, with the potential of diffusing into the carotid artery passing through the sinus cavernous, where diffusing through the rete mirabile. Delivery to the branches of the trigeminal nerve for potential peripheral action on the nerves (analgesics), uptake and transport along the nerves to central ganglion and potentially into the CNS or with reflectory actions in other parts of the face or CNS. Improved deposition of drugs in the middle meatus and infundibulum which includes the sinus ostia. This region plays a key role in ventilation of the sinuses and in the development of sinus pathology and consequently for the treatment of pathology in this region. Delivery of topically-acting substances, such as decongestants, steroids and antihistamines, which can reduce the mucosal swelling in the entrances to and in the narrow slit like passages of the upper part of the nose in order to improve olfaction or reverse anosmia.

Preferred embodiments of the present invention will now be described hereinbelow by way of example only with reference to the accompanying drawings, in which:

FIG. 1(*a*) schematically illustrates the anatomy of the upper respiratory tract of a human subject;

Figure 1A:
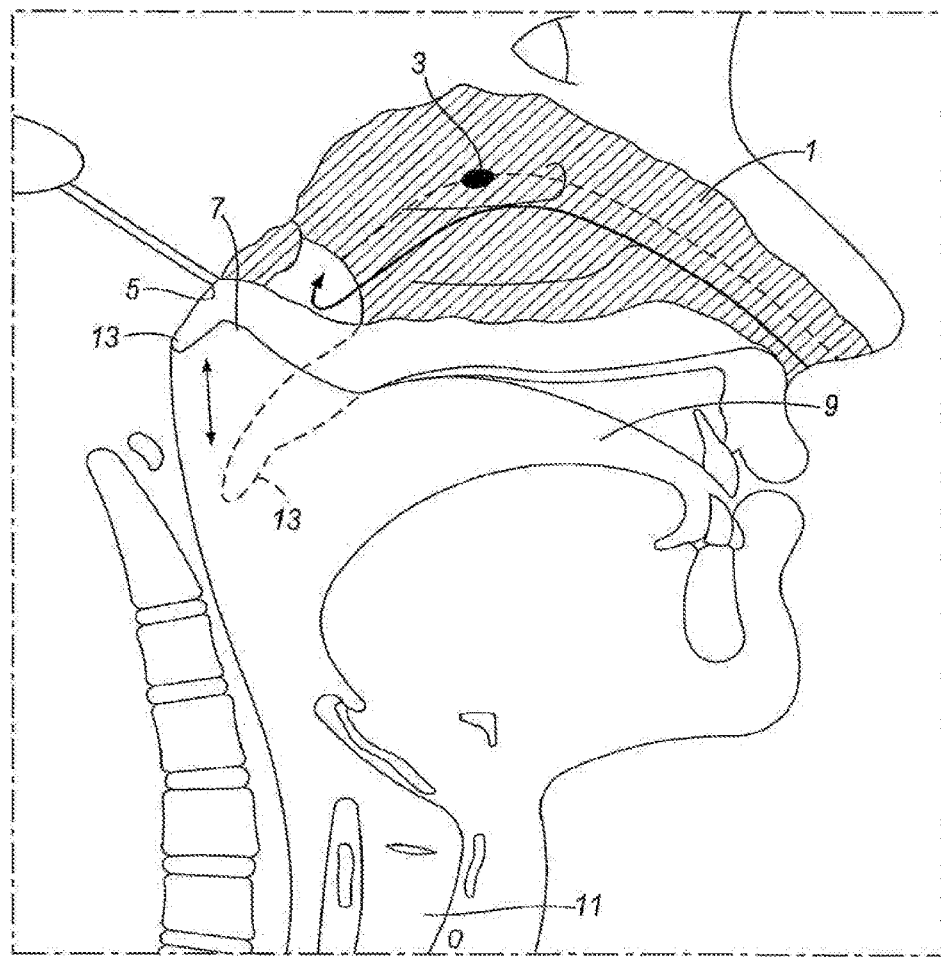
FIG. 1(*b*) illustrates the segmentation of a nasal cavity in accordance with a preferred embodiment of the present invention.
Figure 2:
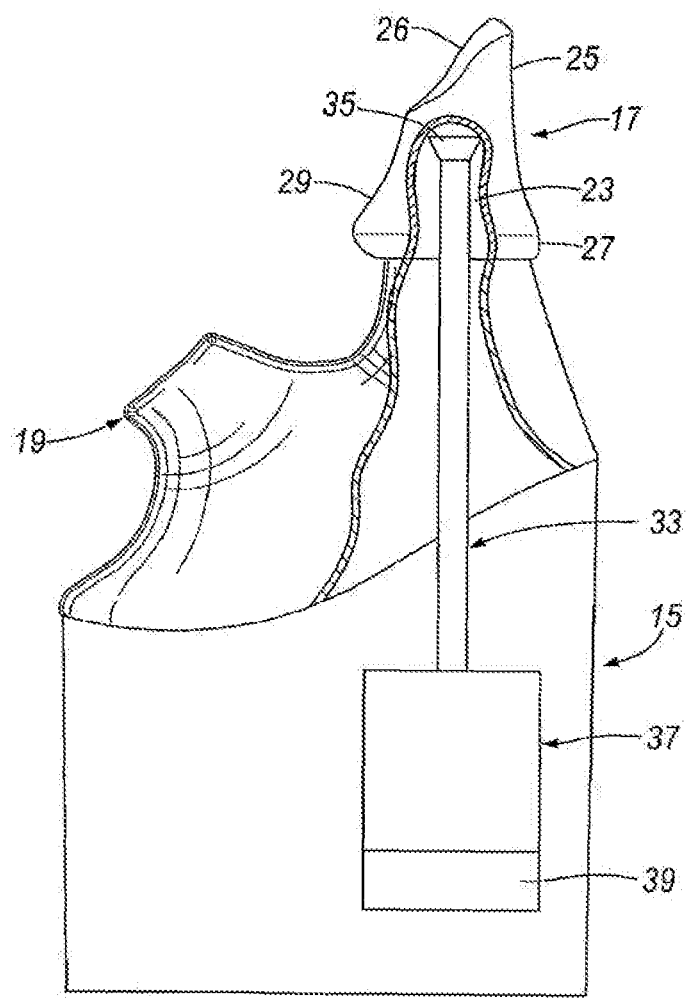
FIG. 2 illustrates a nasal delivery device in accordance with a first embodiment of the present invention.
Figure 3A:
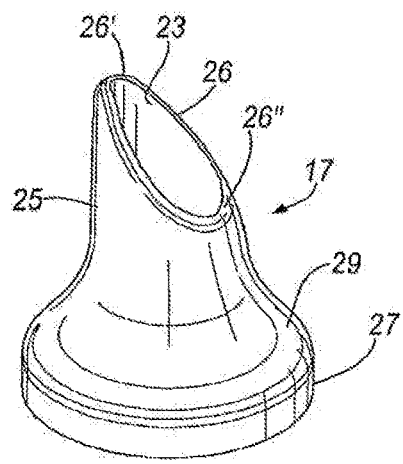
Figure 3B:
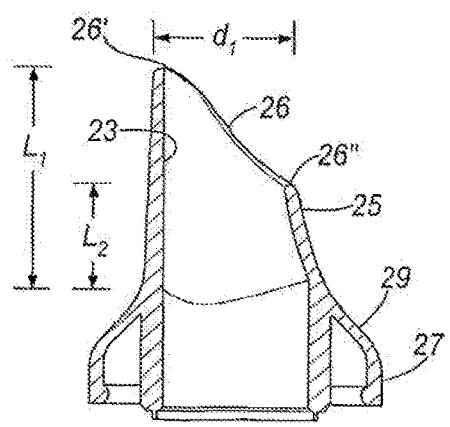
Figure 14:
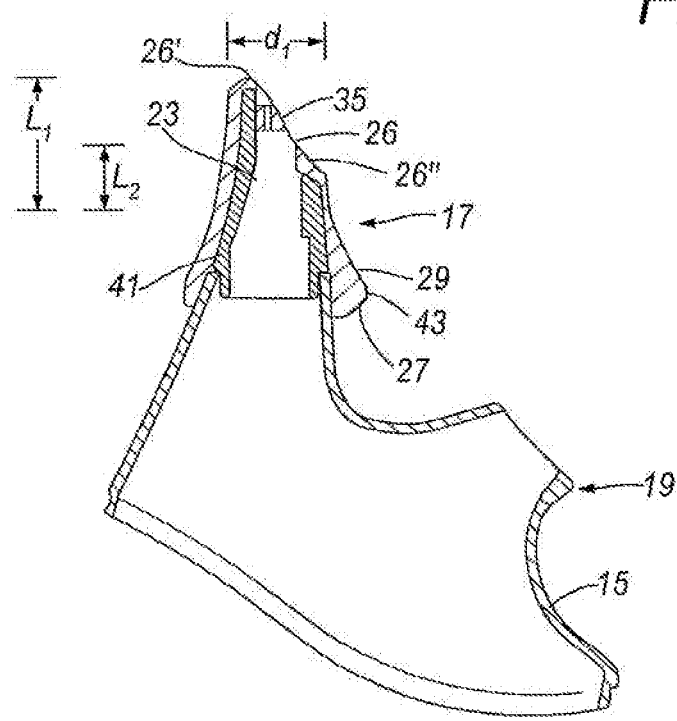
Figure 15A:
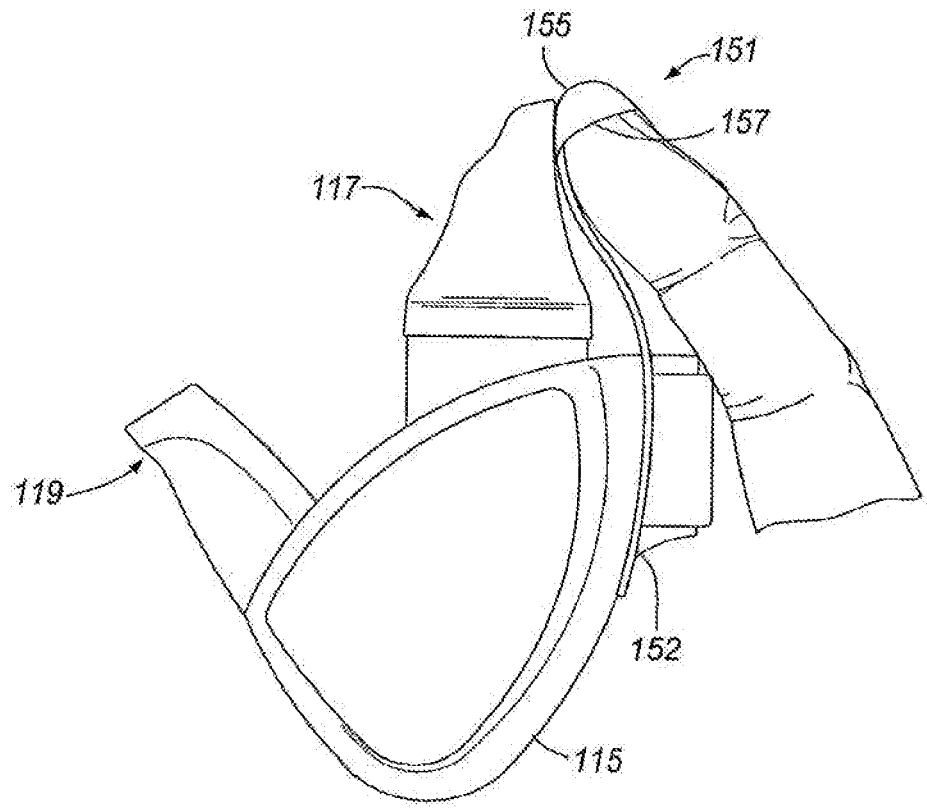
Figure 15B:
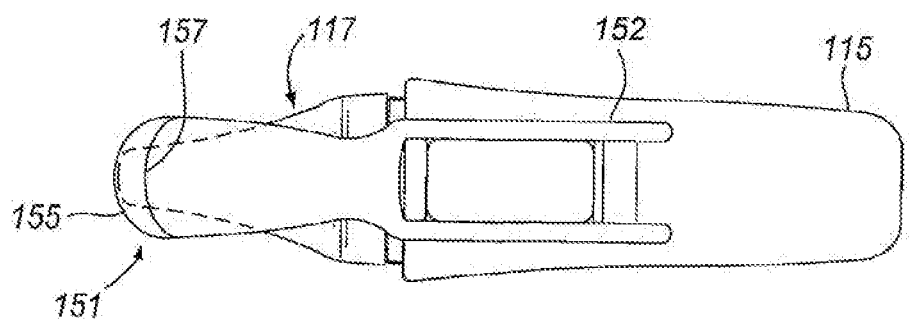
Figure 16:
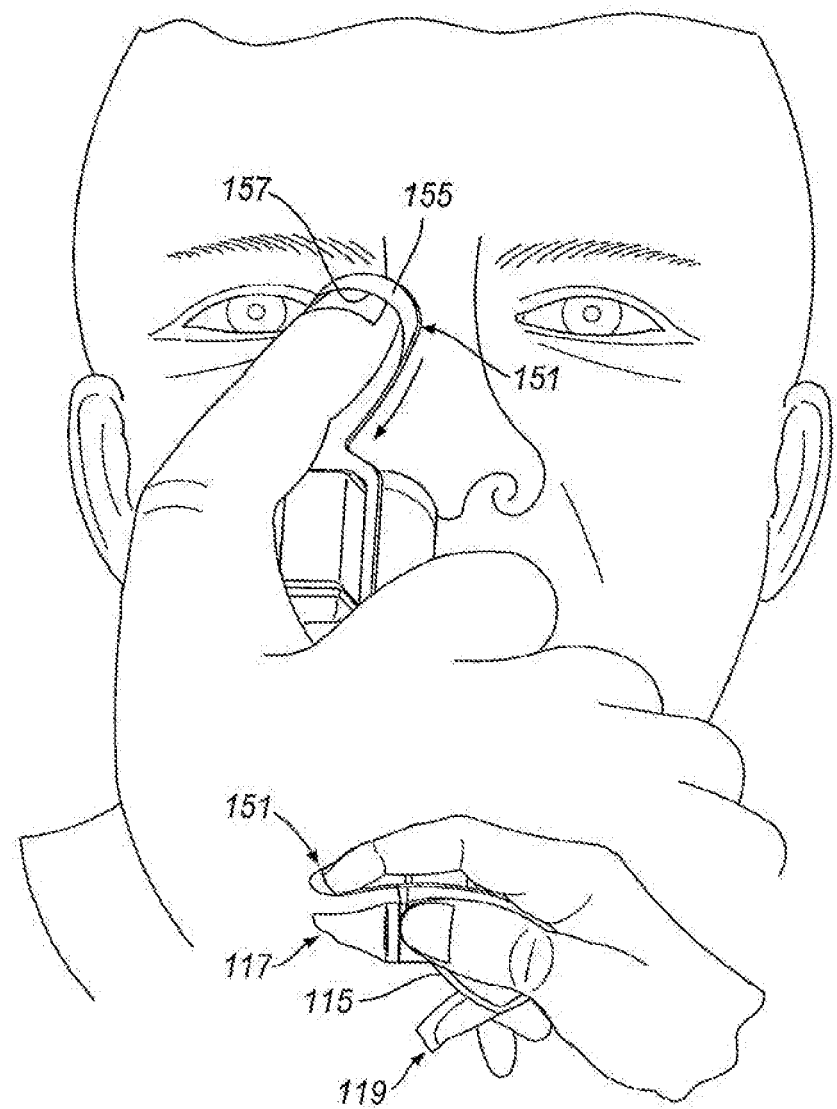
Figure 17A:
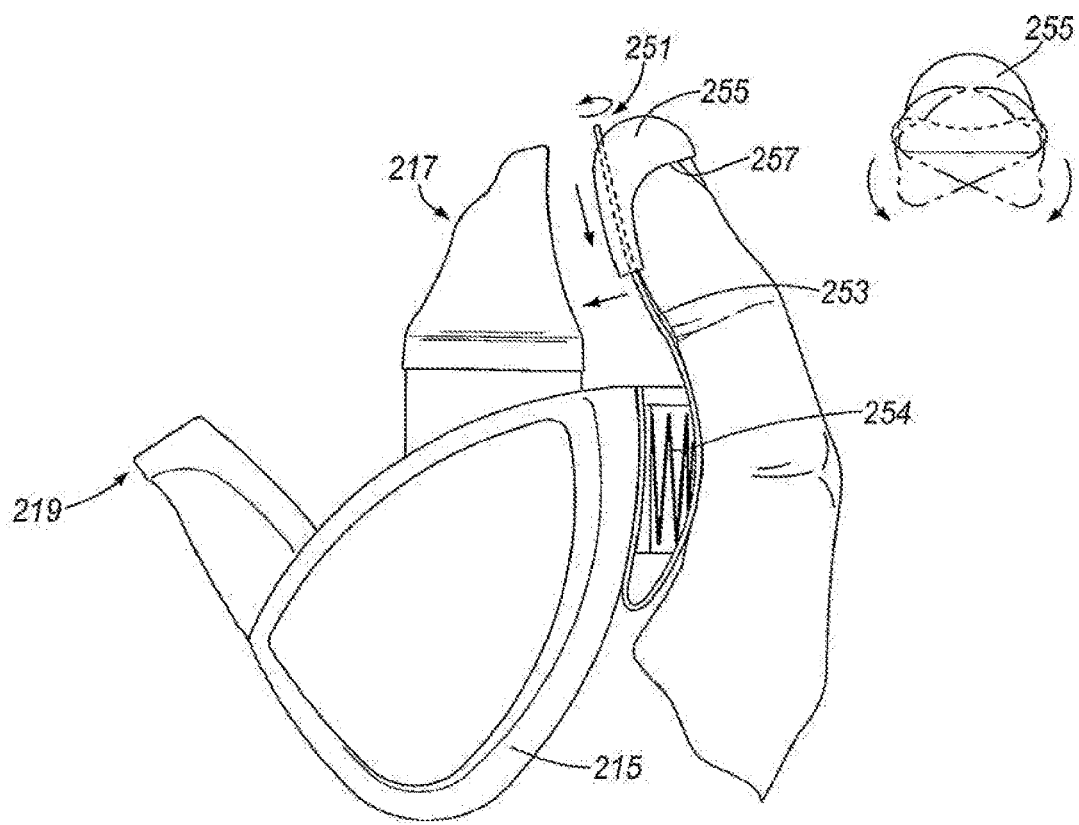
Figure 17B:
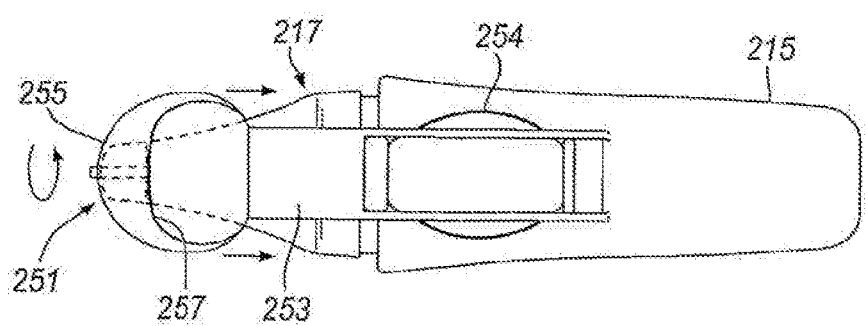
Figure 18:
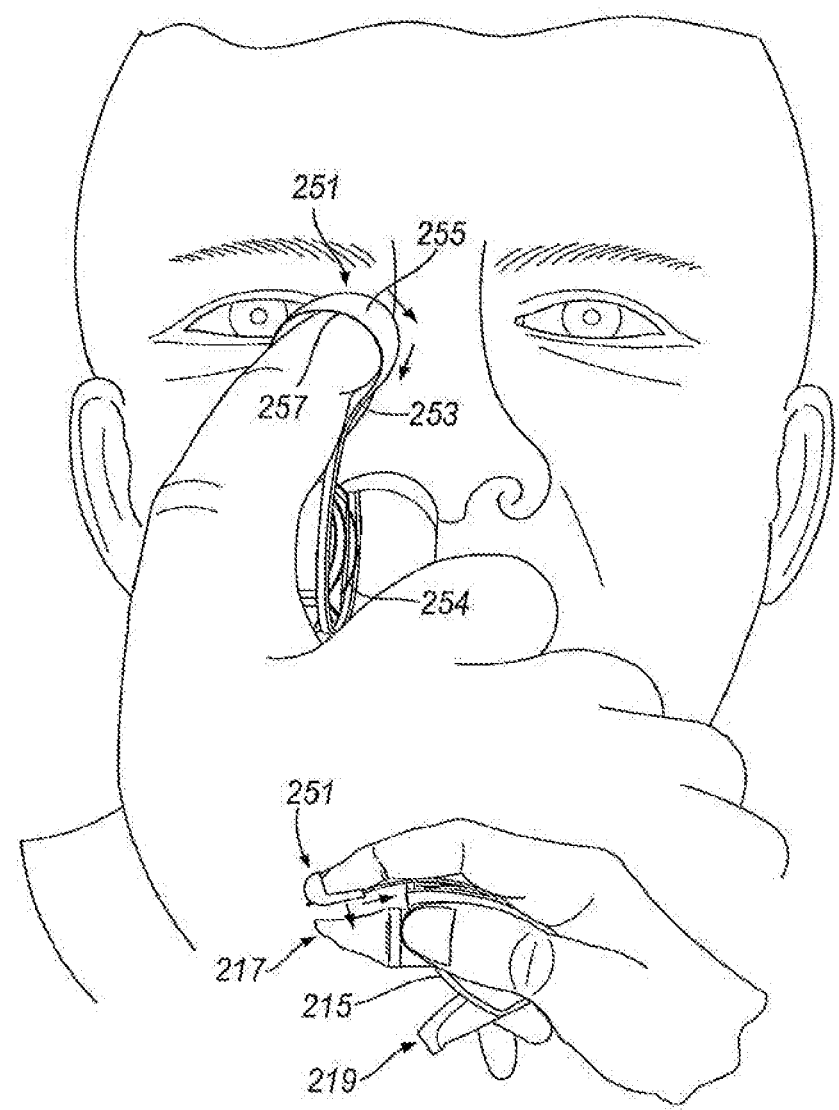
Figure 19A:
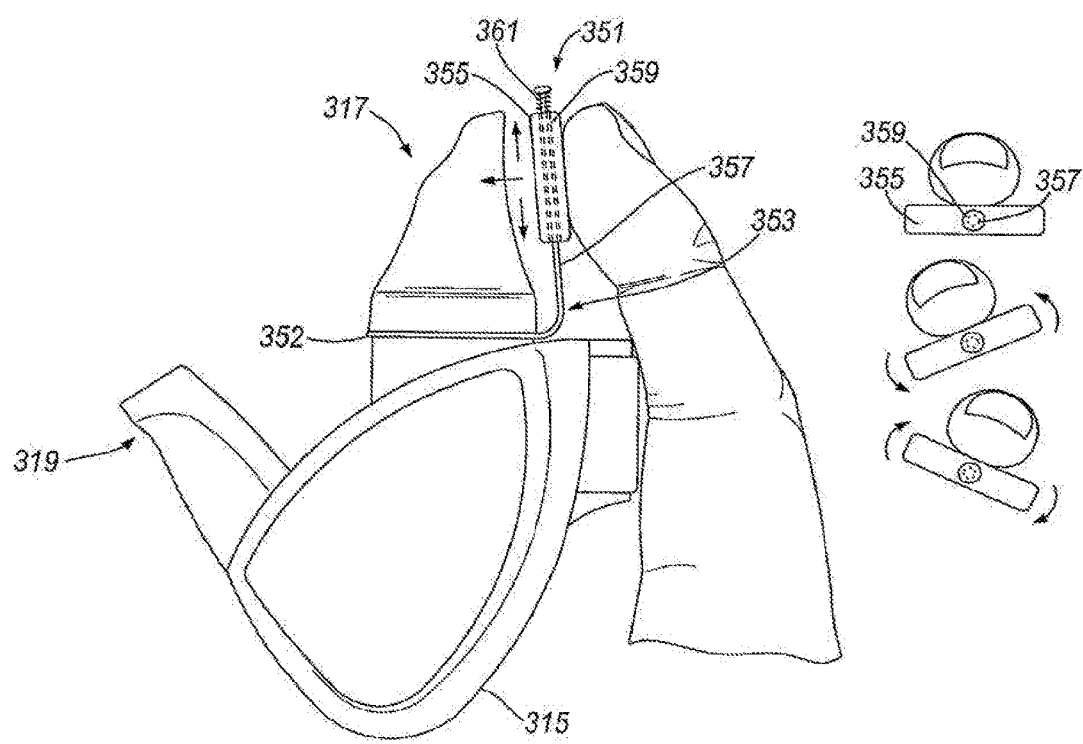
Figure 19B:
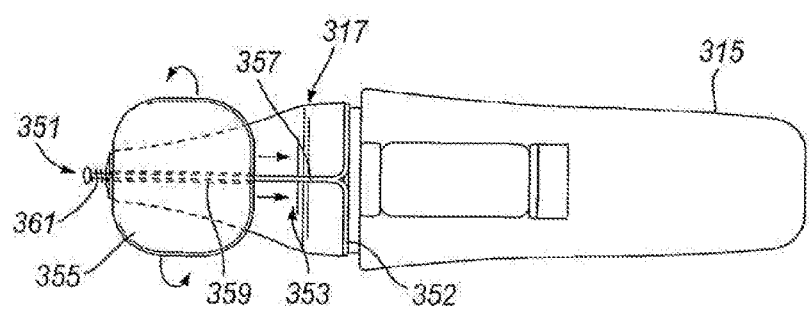
Figure 20:
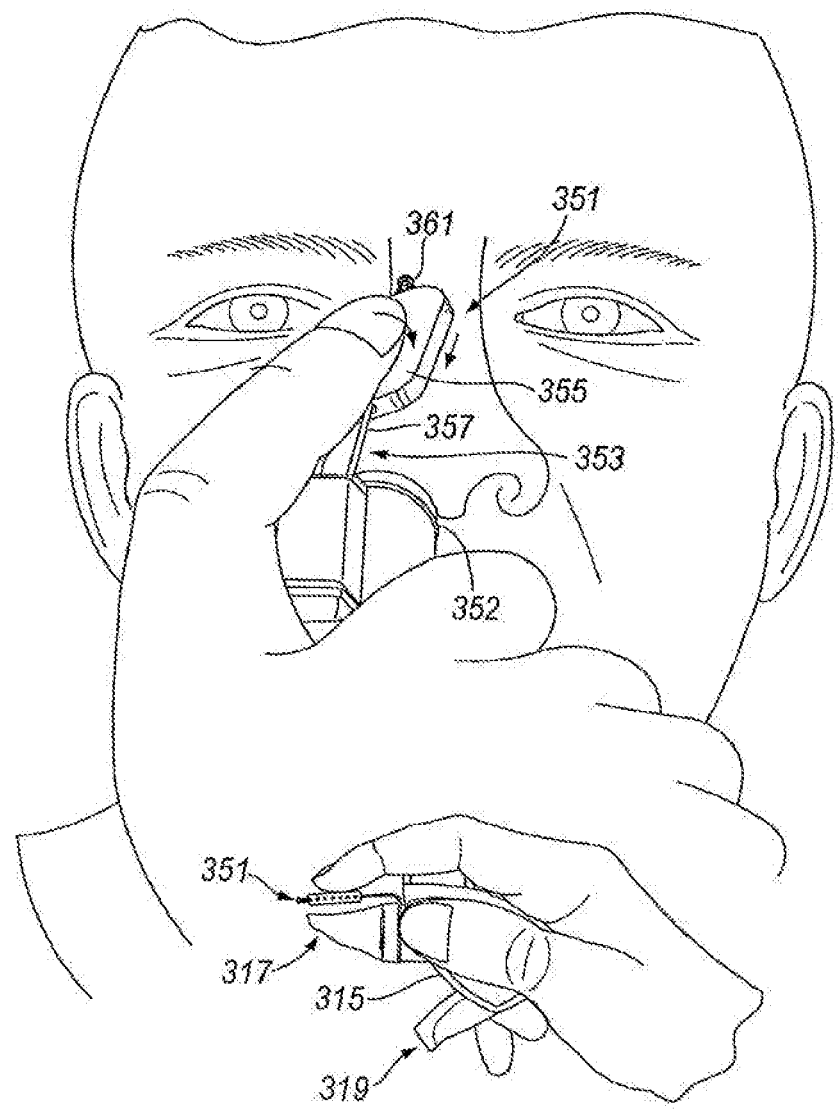
Figure 21A:
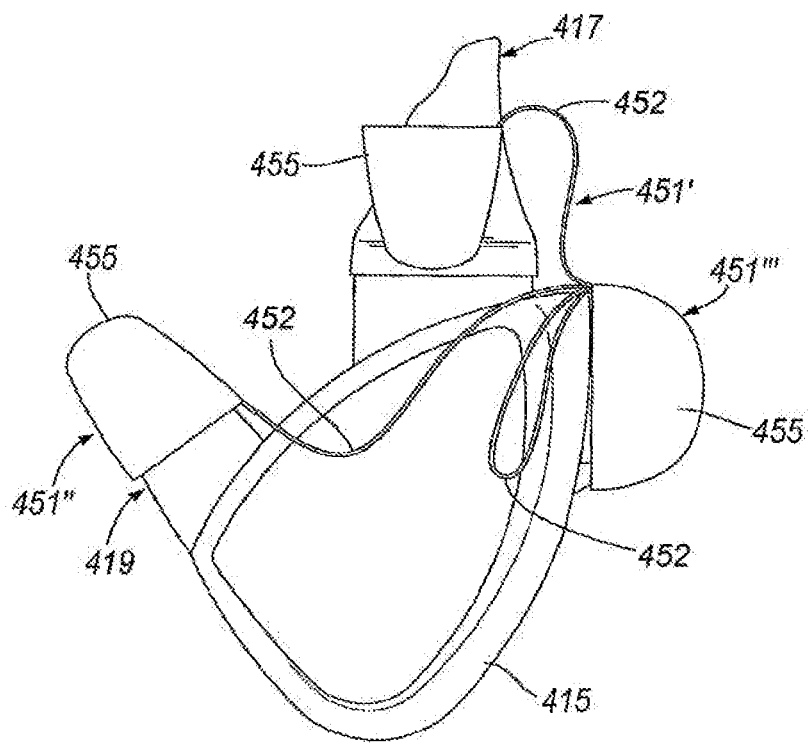
Figure 21B:
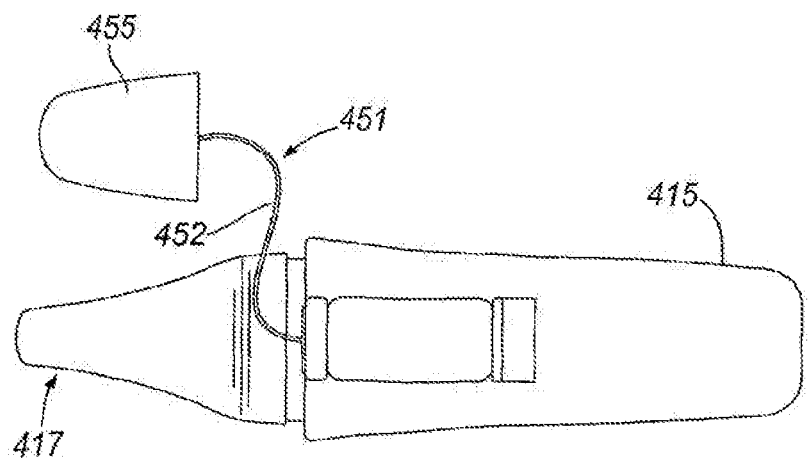
Figure 22:
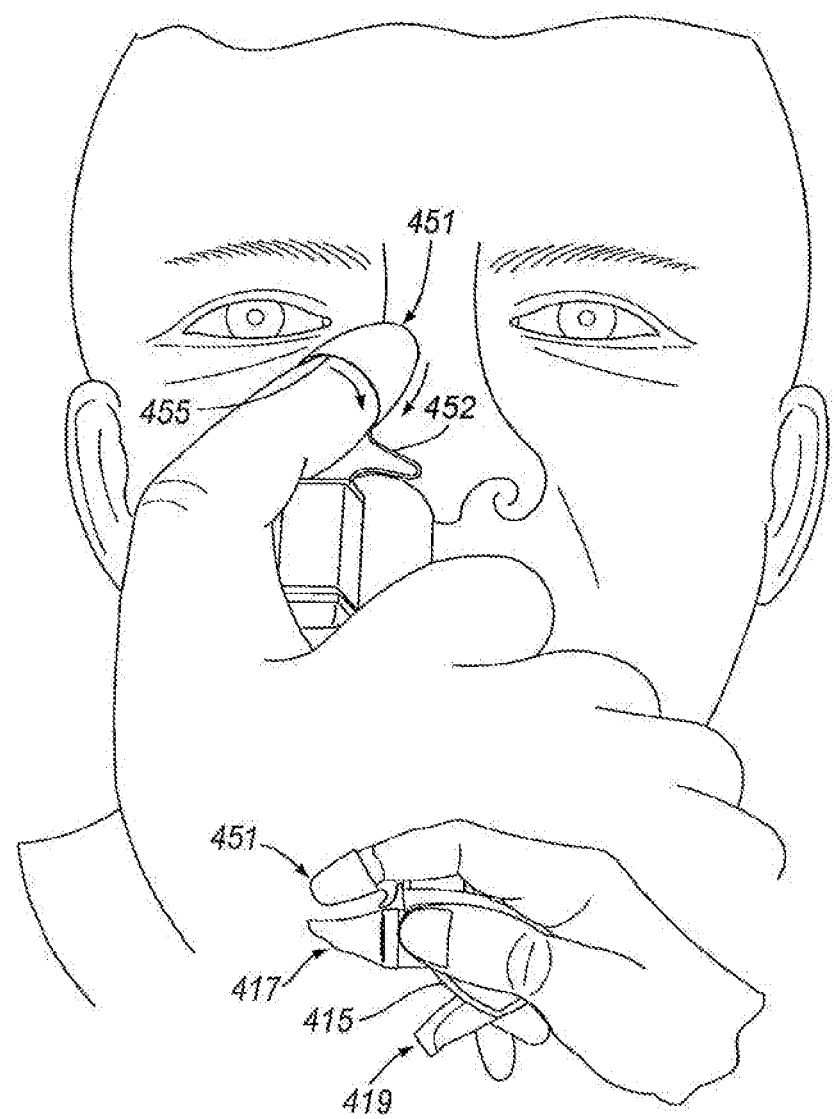
Figure 23A:
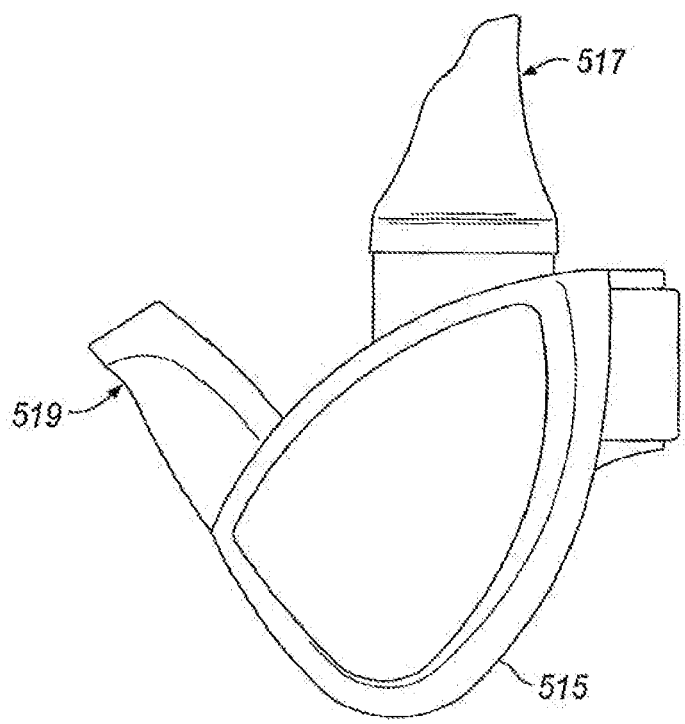
Figure 23B:
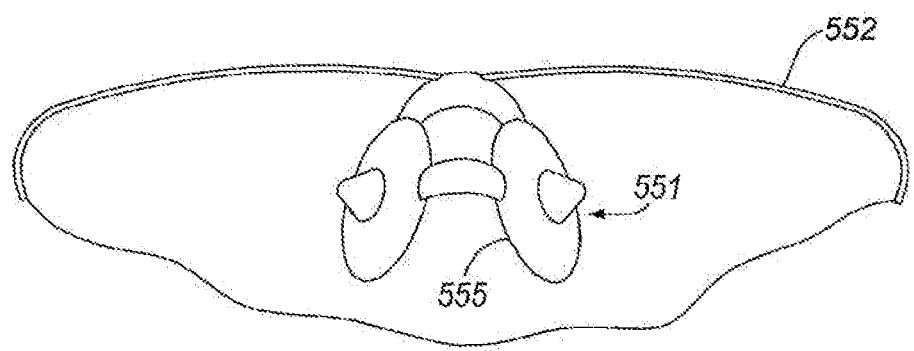
Figure 24:
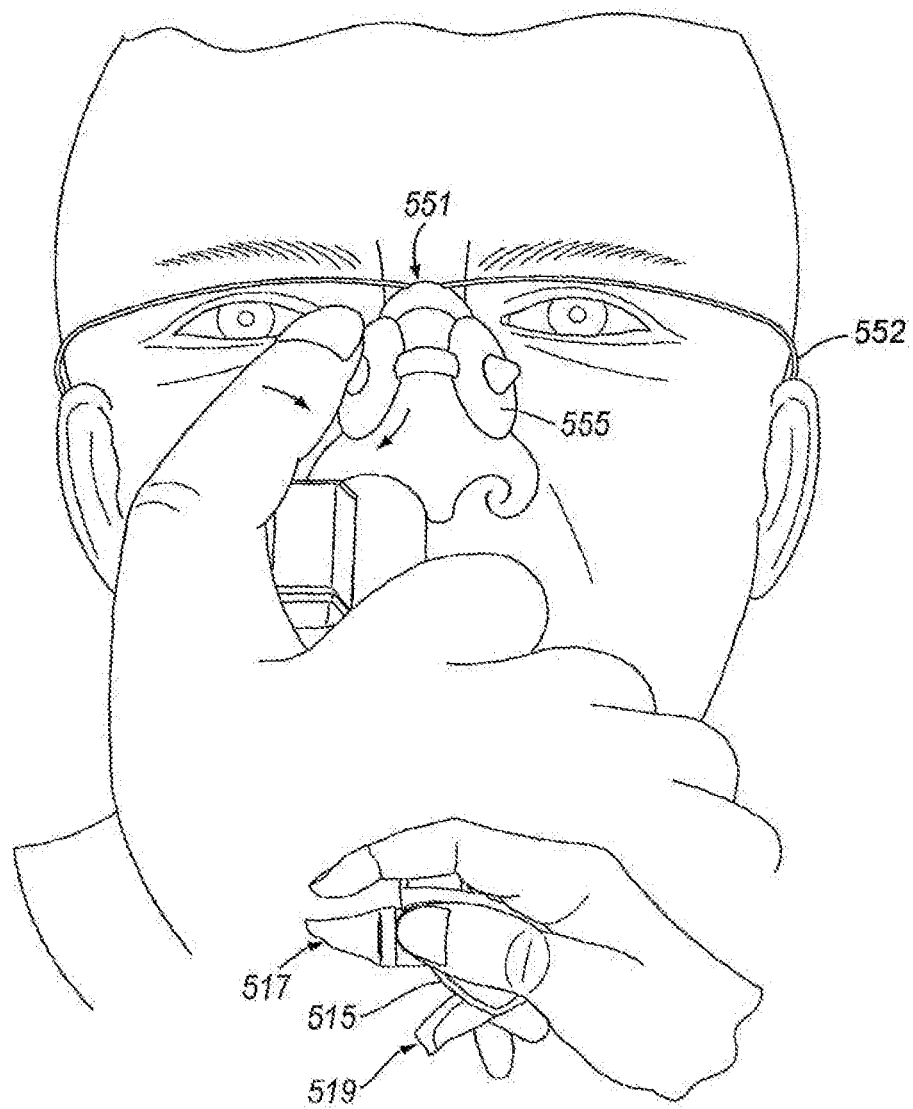
Figure 25A:
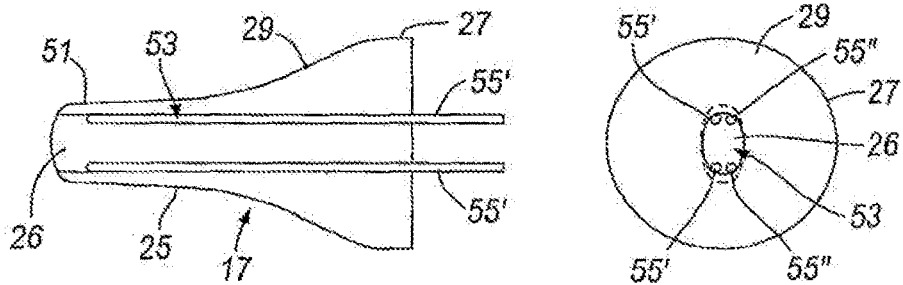
Figure 25B:
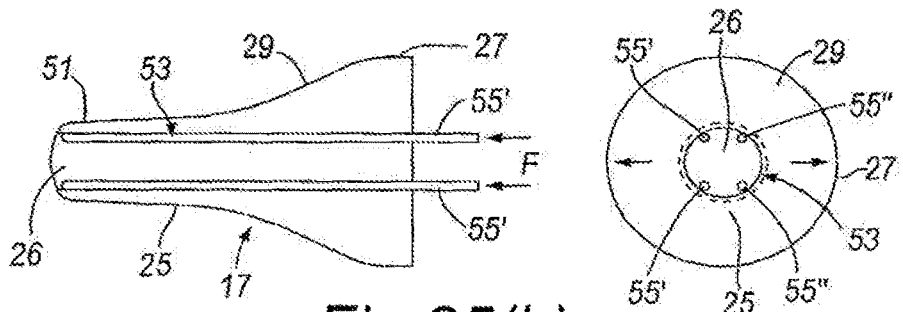
Figure 26A:
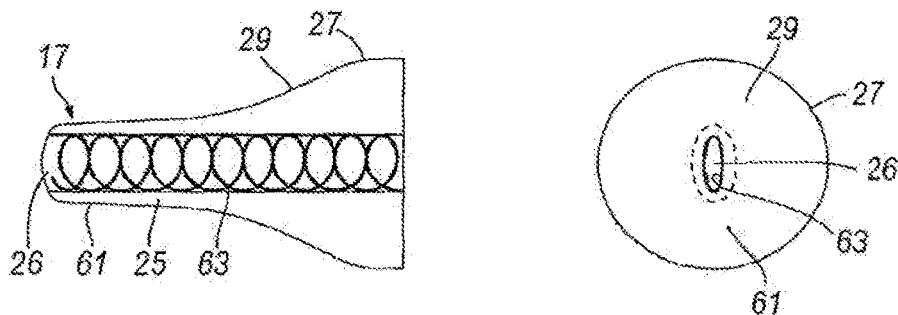
Figure 26B:
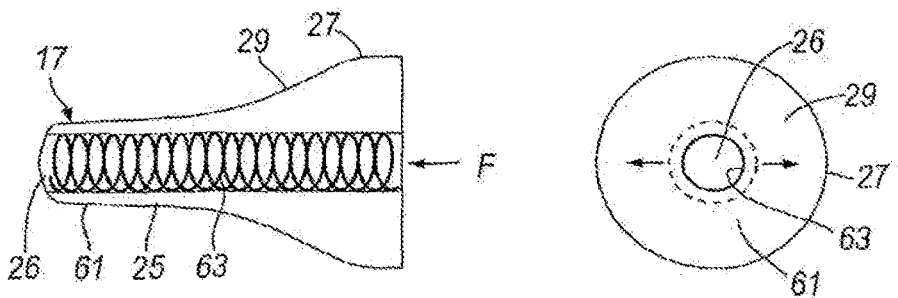
Figure 27A:
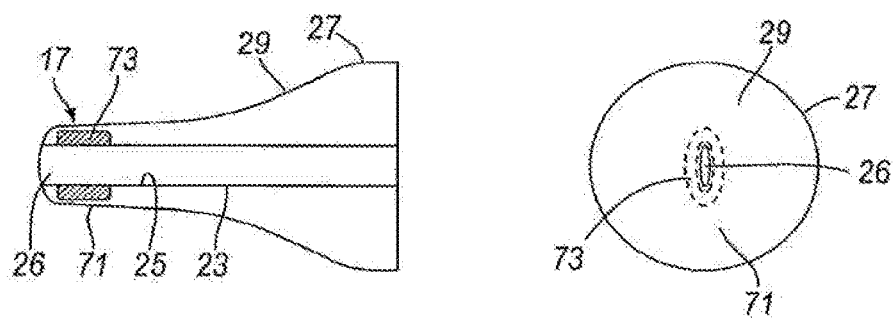
Figure 27B:
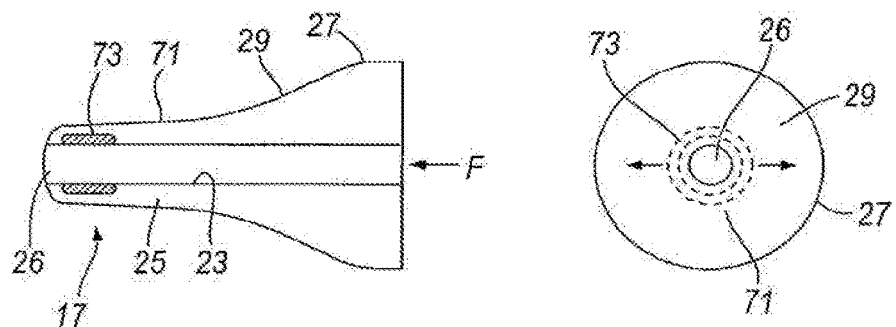

FIGS. 3(*a*) to (*c*) illustrate perspective, vertical sectional and plan views of the nosepiece of the delivery device of FIG. 2;

FIGS. 4(*a*) to (*f*) illustrate the operation of the nasal delivery device of FIG. 2;

FIGS. 5(*a*) to (*c*) illustrate a first modified nosepiece for the delivery device of FIG. 2;

FIGS. 6(*a*) to (*c*) illustrate a second modified nosepiece for the delivery device of FIG. 2;

FIGS. 7(*a*) to (*c*) illustrate a third modified nosepiece for the delivery device of FIG. 2;

FIGS. 8(*a*) to (*c*) illustrate a fourth modified nosepiece for the delivery device of FIG. 2;

FIGS. 9(*a*) to (*c*) illustrate a fifth modified nosepiece for the delivery device of FIG. 2;

FIGS. 10(*a*) to (*c*) illustrate a sixth modified nosepiece for the delivery device of FIG. 2;

FIGS. 11(*a*) to (*c*) illustrate a seventh modified nosepiece for the delivery device of FIG. 2;

FIGS. 12(*a*) to (*c*) illustrate an eighth modified nosepiece for the delivery device of FIG. 2;

FIGS. 13(*a*) to (*d*) illustrate side, front, plan and sectional (along section I-I in FIG. 13(*b*)) views of a ninth modified nosepiece for the delivery device of FIG. 2;

FIG. 14 illustrates a tenth modified nosepiece for the delivery device of FIG. 2, as a further modification of the delivery device of FIG. 13;

FIGS. 15(*a*) and (*b*) illustrate side and end views of a nasal delivery device in accordance with a second embodiment of the present invention;

FIG. 16 illustrates the operation of the delivery device of FIG. 15;

FIGS. 17(*a*) and (*b*) illustrate side and end views of a nasal delivery device in accordance with a third embodiment of the present invention;

FIG. 18 illustrates the operation of the delivery device of FIG. 17;

FIGS. 19(*a*) and (*b*) illustrate side and end views of a nasal delivery device in accordance with a fourth embodiment of the present invention;

FIG. 20 illustrates the operation of the delivery device of FIG. 19;

FIGS. 21(*a*) and (*b*) illustrate side and end views of a nasal delivery device in accordance with a fifth embodiment of the present invention;

FIG. 22 illustrates the operation of the delivery device of FIG. 21;

FIGS. 23(*a*) and (*b*) illustrate side and end views of a nasal delivery device in accordance with a sixth embodiment of the present invention;

FIG. 24 illustrates the operation of the delivery device of FIG. 23;

FIG. 25(*a*) illustrates a further modification of the nosepiece of the delivery device of FIG. 2, in an inoperative or rest state;

FIG. 25(*b*) illustrates the nosepiece of FIG. 25(*a*) following insertion into a nasal cavity of a subject;

FIG. 26(*a*) illustrates a yet further modification of the nosepiece of the delivery device of FIG. 2, in an inoperative or rest state;

FIG. 26(*b*) illustrates the nosepiece of FIG. 26(*a*) following insertion into a nasal cavity of a subject;

FIG. 27(*a*) illustrates a still yet further modification of the nosepiece of the delivery device of FIG. 2, in an inoperative or rest state; and FIG. 27(*b*) illustrates the nosepiece of FIG. 27(*a*) following insertion into a nasal cavity of a subject and inflation to open the delivery aperture.

FIGS. 2 and 3 illustrate a nasal delivery device in accordance with a first embodiment of the present invention.

The delivery device comprises a housing 15, a nosepiece 17 for fitting in a nasal cavity of a subject, and a mouthpiece 19 through which the subject exhales to actuate the delivery device.

The nosepiece 17 is attached to the housing 15 and defines a delivery channel 23 which is in fluid communication with the mouthpiece 19 such that an air flow is delivered into and through the nasal airway of the subject on exhalation by the subject through the mouthpiece 19.

As particularly illustrated in FIGS. 3(*a*) to (*c*), the nosepiece 17 comprises a tip element 25 for insertion into the nasal cavity of the subject, which includes a delivery aperture 26 from which substance is delivered into the nasal cavity of the subject, and a base section 27 from which the tip element 25 extends, in this embodiment substantially axially to the longitudinal axis of the nosepiece 17.

In this embodiment the tip element 25 is of asymmetric, elongate section, in having a dimension d1 in a first, sagittal direction which is greater than a dimension d2 in a second, lateral direction orthogonal to the first, sagittal direction.

With this configuration, on insertion of the nosepiece 17 into the nasal cavity of the subject, the longer, sagittal section of the tip element 25 of the nosepiece 17 becomes aligned in the sagittal plane and acts to engage upper and lower walls of the nasal cavity of the subject and cause the expansion of the nasal cavity in the vertical, sagittal plane, in particular the upper wall of the nasal cavity of the subject, which is a fleshy structure, as compared to the lower wall of the nasal cavity of the subject, which is a relatively-hard structure, and also position the nosepiece 17 in the nasal cavity of the subject, with the lower wall of the nasal cavity of the subject, in being a relatively-hard structure, acting as a reference for the expansion. This expansion further acts to tension the lateral walls of the nasal cavity of the subject which defines the nasal valve, which causes the lateral walls of the nasal cavity to be urged into sealing contact with the nosepiece 17.

In this embodiment the distal end of the tip element 25 is, at least in part, tapered, such as to be inclined, here in the sagittal plane, to the longitudinal axis of the nosepiece 17. With this configuration, the delivery aperture 26 extends both laterally across the tip element 25 and along a longitudinal extent of the tip element 25. The present inventors have recognized that this configuration is particularly advantageous in ensuring the delivery of substance from the nosepiece 17 when inserted substantially in any orient into the nasal cavity of a subject. The present inventors have found that the provision of the delivery aperture 26 in a conventional sense, that is, in an orthogonal relation to the longitudinal axis of the nosepiece 17, can lead to obstruction of the delivery aperture 26 by soft tissue within the nasal cavity, and that this problem is remarkably overcome by providing that the delivery aperture 26 is inclined to the longitudinal axis of the nosepiece 17, thereby in effect extending along a length of the longitudinal extent of the tip element 25.

Figure 3C:
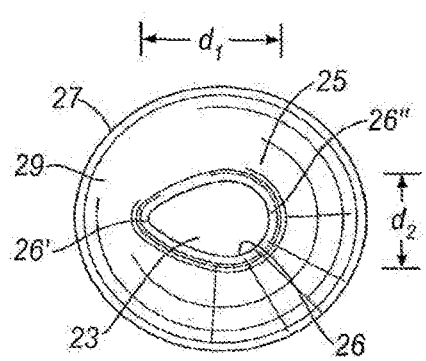

In this embodiment the delivery aperture 26 has an asymmetric shape in plan view, as illustrated in FIG. 3(c), with the delivery aperture 26 having a sharper, narrower section 26' adjacent one, the forwardmost, end of the tip element 25 and a wider, flatter section 26" adjacent the other, rearwardmost, end of the tip element 25. This configuration acts to provide for greater air flow through the delivery aperture 26 at a location spaced rearwardly of the forwardmost section of the tip element 25, which represents that section which is most likely to abut soft tissue in the nasal cavity of the subject.

In this embodiment the base section 27 defines a shoulder 29, which provides both a seal with the nares of the nostril of the subject and determines the extent of the insertion of the nosepiece 17 into the nasal cavity of the subject. In addition, as will be described in more detail hereinbelow, the shoulder 29 allows for the nare of the nostril of the subject to be gripped thereagainst by a finger of the subject, in fixing the position of the delivery device. The skin of the nose can be particularly slippery due to excreted oils, and the provision of a gripping surface at the shoulder 29 is particularly beneficial. This grip can also be improved by the use of a wipe, such as a tissue, particularly where impregnated with an agent which removes the excreted oils, such as to promote the grip with the skin, or alternatively with a grip enhancer, such as a sticky material, for example, a wax, resin, gel or liquid, which promotes the adhesion with the skin.

In this embodiment the nosepiece 17 is formed as a substantially rigid structure, here formed of a plastics material.

The delivery device further comprises an outlet unit 33 which comprises a nozzle 35 at the distal end thereof, in this embodiment disposed in the nosepiece 17, for delivering substance to the nasal airway of the subject.

In a preferred embodiment the nozzle 35 is configured to extend at least about 2 cm, preferably at least about 3 cm, more preferably at least about 4 cm, and preferably from about 2 cm to about 4 cm, into the nasal cavity of the subject on insertion of the nosepiece 17 into the nasal cavity of the subject.

In this embodiment the nozzle 35 is configured to provide an aerosol spray, either as a liquid or powder aerosol.

In an alternative embodiment the nozzle 35 could be configured to deliver a jet as a column of substance, either as a liquid or powder jet.

In this embodiment the nozzle 35 is configured to deliver a symmetric aerosol spray.

In one embodiment the nozzle 35 is configured to deliver an aerosol spray with a spray angle of not more than about 30°, preferably not more than about 25°, and more preferably not more than about 30°.

In an alternative embodiment the nozzle 35 could be configured to deliver an asymmetric aerosol spray, with the aerosol spray having a significantly greater spray angle in the vertical, sagittal plane than in the horizontal plane. Such an aerosol spray has been found to be particularly advantageous in the delivery of substance to posterior regions of the nasal cavities, in particular the olfactory region.

In a preferred embodiment the spray angle in the vertical, sagittal plane is greater than about 35°, more preferably greater than about 40°, still more preferably greater than about 45° and yet more preferably greater than about 50°.

In a preferred embodiment the spray angle in the horizontal plane is not more than about 35°, more preferably not more than about 30°, still more preferably not more than about 25°, yet more preferably not more than about 20°, and still yet more preferably not more than about 15°.

In one embodiment the aerosol spray could present an elliptical spray zone.

In another embodiment the aerosol spray could present a substantially rectangular spray zone.

The delivery device further comprises a substance supply unit 37 for delivering metered doses of a substance, which is fluidly connected to the nozzle 35 of the outlet unit 33 to deliver substance from the nosepiece 17, in this embodiment as an aerosol spray.

In this embodiment the substance supply unit 37 is a multi-dose unit for delivering a plurality of metered doses of substance. In another embodiment the substance supply unit 37 could be a single-dose unit for delivering a single metered dose of substance.

The substance supply unit 37 is pre-primeable, in this embodiment by loading a resilient element, and includes a breath-actuated release mechanism 39 which, when triggered, releases the resilient element and actuates the substance supply unit 37 to deliver a metered dose of substance through the nozzle 35 of the outlet unit 33.

In this embodiment the release mechanism 39 is configured to cause actuation of the substance supply unit 37 on generation of a predetermined flow rate through the delivery channel 23 of the nosepiece 17.

In another embodiment the release mechanism 39 could be configured to cause actuation of the substance supply unit 37 on generation of a predetermined pressure within the delivery channel 23 of the nosepiece 17.

In a further embodiment the release mechanism 39 could be configured to cause actuation of the substance supply unit 37 on generation of either one of a predetermined flow rate through the delivery channel 23 of the nosepiece 17 or a predetermined pressure within the delivery channel 23 of the nosepiece 17.

In this embodiment the substance supply unit 37 comprises a mechanical delivery pump, in particular a liquid delivery pump or a powder delivery pump, which delivers metered doses of a substance on actuation thereof.

In another embodiment the substance supply unit 37 could comprise an aerosol canister for delivering metered volumes of a propellant, preferably a hydrofluoroalkane (HFA) propellant or the like, containing medicament, either as a suspension or solution.

In another alternative embodiment the substance supply unit 37 could comprise a dry powder delivery unit which delivers metered doses of a substance, as a dry powder, on actuation thereof.

In yet another alternative embodiment the substance supply unit 37 could comprise a nebulizer which delivers metered doses of a substance, as an aerosol spray, on actuation thereof.

Operation of the delivery device will now be described hereinbelow with reference to FIGS. 4(a) to (f) of the accompanying drawings.

Figure 4A:
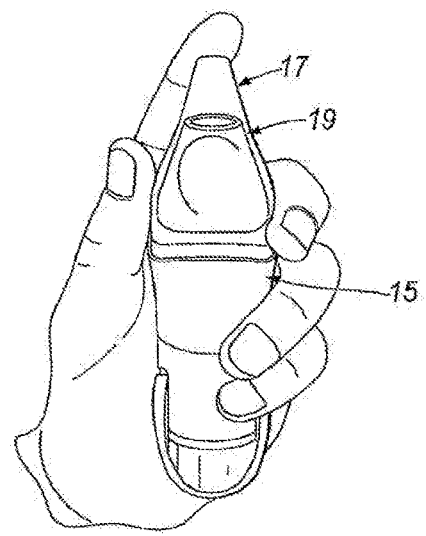

The subject first primes the substance supply unit 37, in this embodiment by loading a biasing element, wipes the nares of his/her nostril with a tissue or the like, and grips the delivery device between the thumb and the second, third and fourth fingers, keeping the first, index finger free, as illustrated in FIG. 4(a).

Figure 4B:
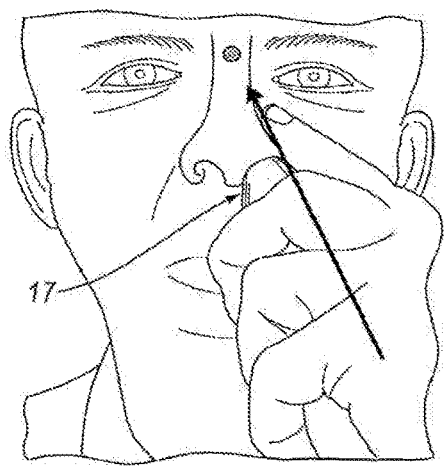

The nosepiece 17 is then inserted into one of the nostrils, in this embodiment the left nostril, with a twisting movement, such as to align the mouthpiece 19 with the mouth of the subject, and then the mouthpiece 19 is gripped in the lips of the subject, as illustrated in FIG. 4(b).

With the nosepiece 17 so inserted into the nasal cavity of the subject, the longer, sagittal section of the tip element 25 is aligned in the sagittal plane and engages upper and lower walls of the nasal cavity of the subject, which engagement causes the expansion of the nasal cavity in the vertical, sagittal plane, in particular the upper wall of the nasal cavity of the subject, which is a fleshy structure, as compared to the lower wall of the nasal cavity of the subject, which is a relatively-hard structure, and also positions the nosepiece 17 in the nasal cavity of the subject, with the lower wall of the nasal cavity of the subject, in being a relatively-hard structure, acting as a reference for the expansion. This expansion acts to prevent the bulging of the fleshy structure which can cause partial or full obstruction of the nasal valve and further acts to tension the lateral walls of the nasal cavity of the subject which defines the nasal valve, which causes the lateral walls of the nasal cavity to be urged into sealing contact with the nosepiece 17.

The subject then extends his/her index finger adjacent the nare of the nostril, such that the index finger is directed to a point between the eyes and the tip of the finger is broadly aligned with the distal end of the nosepiece 17 which is located within the nasal cavity, as illustrated in FIG. 4(b). In an alternative embodiment the free finger could be another finger other than the index finger.

Figure 4C:
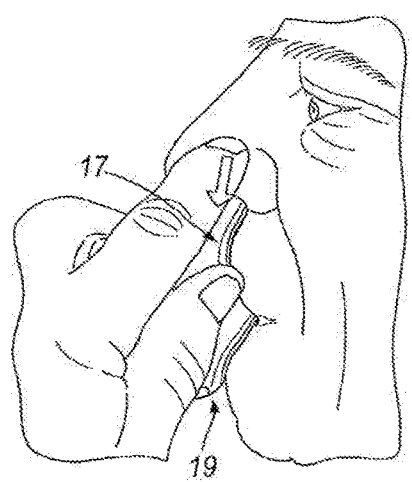

The index finger is then pressed against the skin of the nose, such as to press the nare of the nostril against the nosepiece 17, and gently retracted, such as to pull the nare of the nostril onto the shoulder 29 of the nosepiece 17, as illustrated in FIG. 4(c). This action acts to straighten the flow path and improve access beyond the nasal valve. In one embodiment the skin of the nose can be cleaned by the use of a wipe, which can be impregnated with a cleaning agent to promote the removal of the secreted oils, or alternatively a grip-enhancing agent can be applied to the skin of the nose to promote the grip therewith.

The subject then begins to exhale through the mouthpiece 19, which exhalation acts to close the oropharyngeal velum of the subject and drive an air flow through the delivery channel 23 of the nosepiece 17, with the air flow passing into the one nasal cavity, around the posterior margin of the nasal septum and out of the other nasal cavity, thereby achieving a bi-directional air flow through the nasal airway of the subject.

In this embodiment, when the flow rate developed through the delivery channel 23 of the nosepiece 17 reaches a predetermined value, the release mechanism 39 is triggered to actuate the substance supply unit 37 to deliver a metered dose of a substance to the nozzle 35 of the outlet unit 33 and into the nasal cavity of the subject, in this embodiment as an aerosol spray. In an alternative embodiment the release mechanism 39 could be triggered on the generation of a predetermined pressure in the delivery channel 23 of the nosepiece 17.

Following exhalation, the subject then releases the mouthpiece 19 and the nosepiece 17 is withdrawn from the nasal cavity of the subject.

In one embodiment, where the delivery device is a single-dose device, the device can be discarded.

In another embodiment, as in this embodiment, where the delivery device is a multi-dose device, the device is ready for further use following priming of the substance supply unit 37.

Figure 4D:
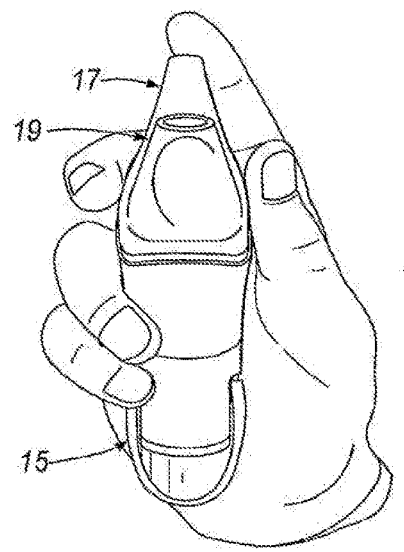
Figure 4E:
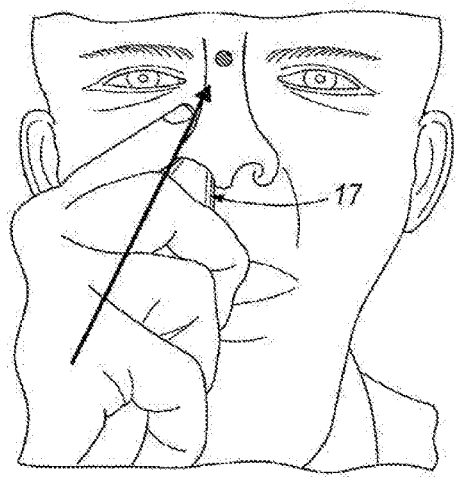
Figure 4F:
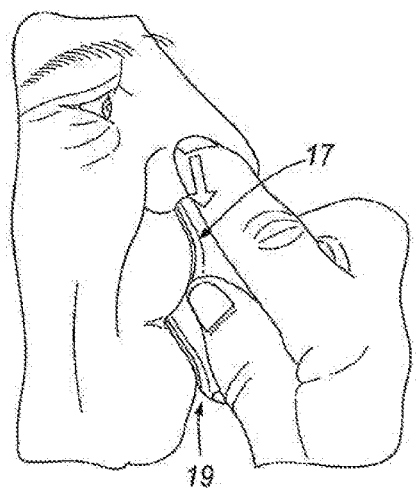

In this embodiment a second dose of substance is delivered into the other nostril, here the right nostril, in the same manner as described hereinabove and illustrated in FIGS. 4(d) to (f).

Figure 5A:
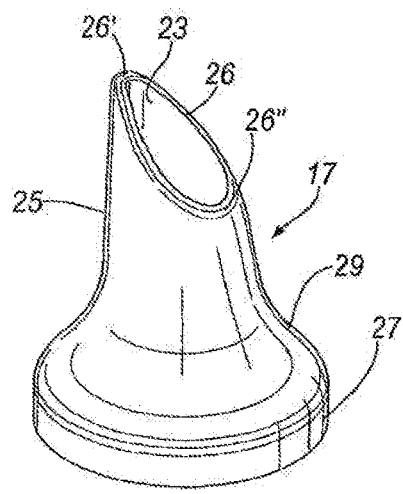
Figure 5B:
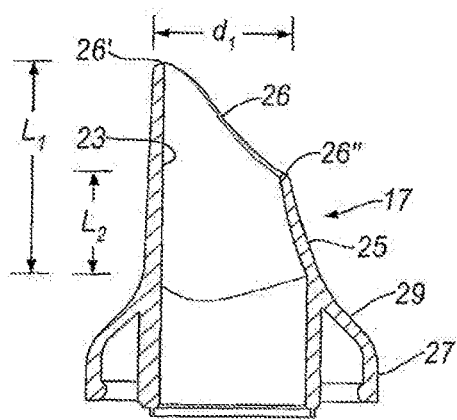
Figure 5C:
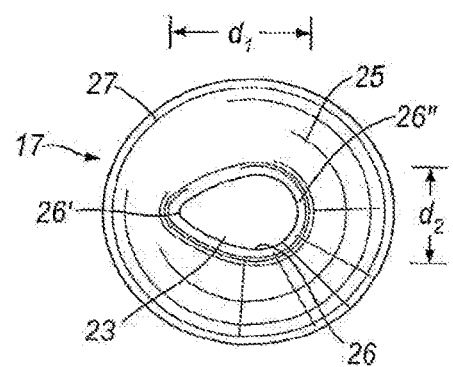

FIGS. 5(a) to (c) illustrate a modified nosepiece 17 for the delivery device of the above-described embodiment.

In this embodiment the tip element 25 has a greater length than the tip element 25 of the above-described embodiment.

Figure 6A:
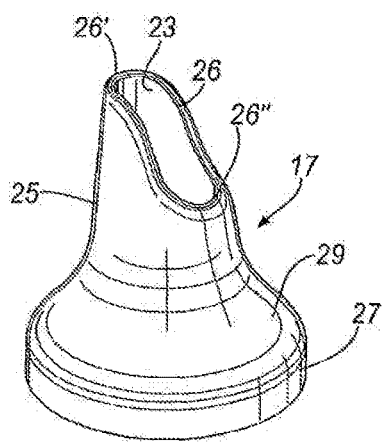
Figure 6B:
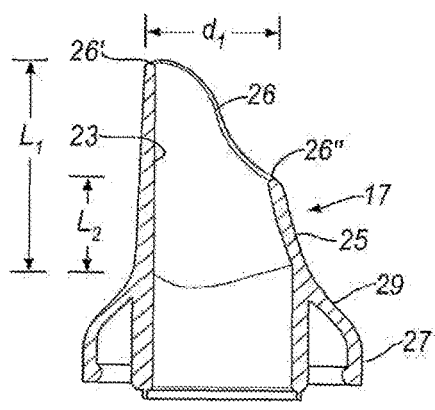
Figure 6C:
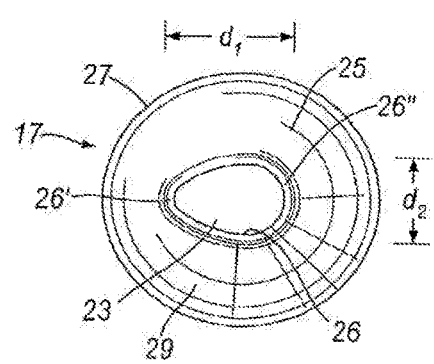

FIGS. 6(a) to (c) illustrate another modified nosepiece 17 for the delivery device of the above-described embodiment.

In this embodiment the ratio of the lengths of the sagittal sections 26', 26" of the tip element 25 is greater than that of the above-described embodiment, such as to provide a more elongate delivery aperture 26. In this embodiment the length l1 of the forwardmost sagittal section 26' is greater than twice the length l2 of the rearwardmost sagittal section 26".

Further, in this embodiment the tip element 25 is shaped such that the delivery aperture 26 comprises an orthogonal section adjacent the forwardmost sagittal section 26'.

Figure 7A:
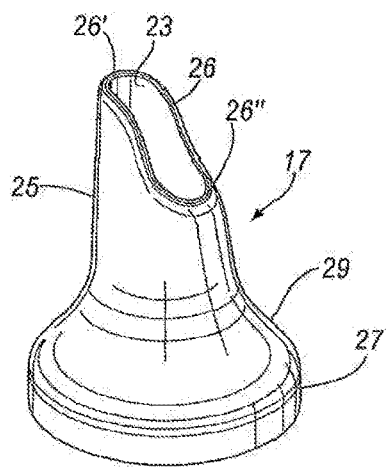
Figure 7B:
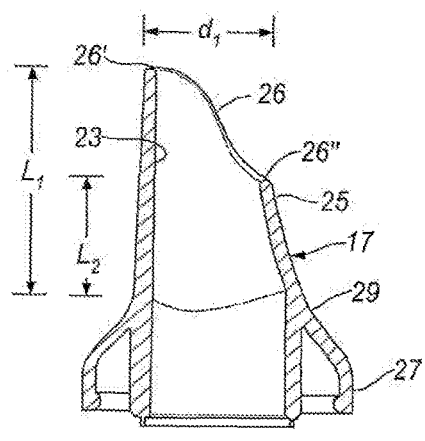
Figure 7C:
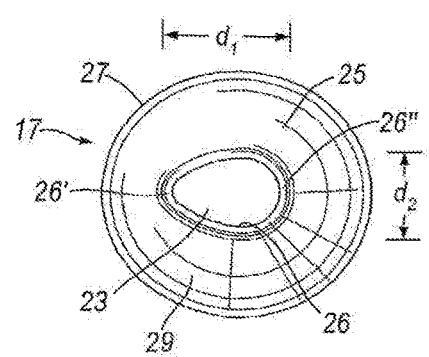

FIGS. 7(a) to (c) illustrate a further modified nosepiece 17 for the delivery device of the above-described embodiment.

In this embodiment the tip element 25 has a greater length than the tip element 25 of the embodiment of FIGS. 6(a) to (c).

Figure 8A:
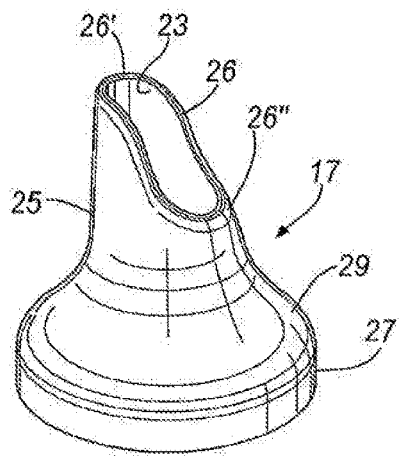
Figure 8B:
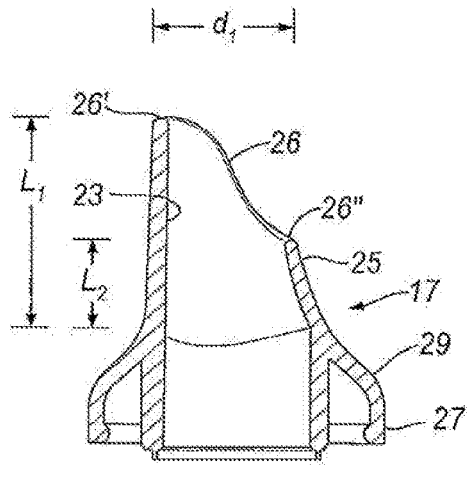
Figure 8C:
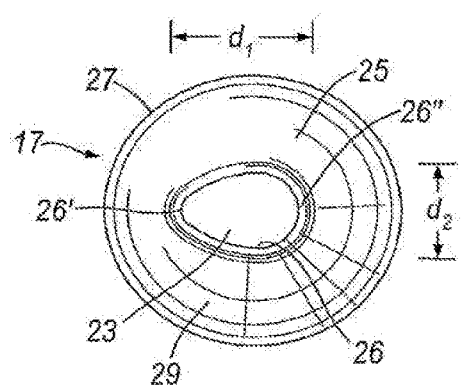

FIGS. 8(a) to (c) illustrate a yet further modified nosepiece 17 for the delivery device of the above-described embodiment.

In this embodiment the tip element 25 has a greater width at the proximal end thereof than the tip element 25 of the embodiment of FIGS. 6(a) to (c). With this configuration, the shoulder 29 acts to promote sealing with the nares of the nostril of the subject.

Further, in this embodiment the length l1 of the forwardmost sagittal section 26' is about twice the length l2 of the rearwardmost sagittal section 26".

Figure 9A:
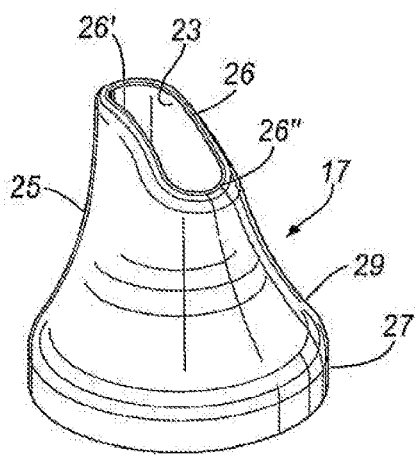
Figure 9B:
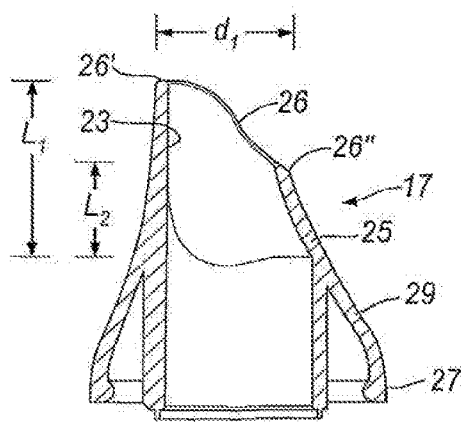
Figure 9C:
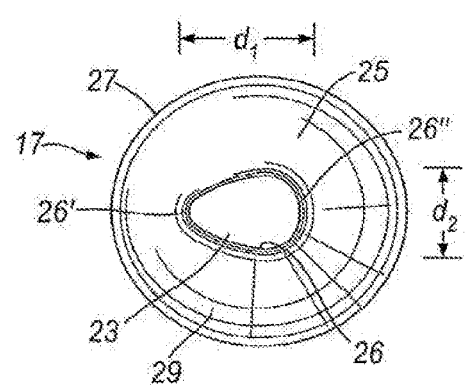

FIGS. 9(a) to (c) illustrate a still further modified nosepiece 17 for the delivery device of the above-described embodiment.

In this embodiment the tip element 25 has a wider, frusto-conical section than the tip element 25 of the above-described embodiment. With this configuration, the shoulder 29 acts to promote sealing with the nares of the nostril of the subject deeper in the nasal cavity.

Further, in this embodiment the length l1 of the forwardmost sagittal section 26' is less than twice the length l2 of the rearwardmost sagittal section 26".

Figure 10A:
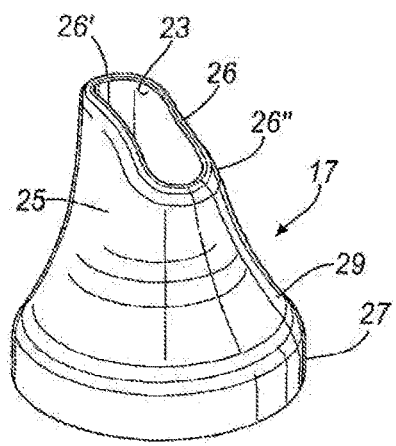
Figure 10B:
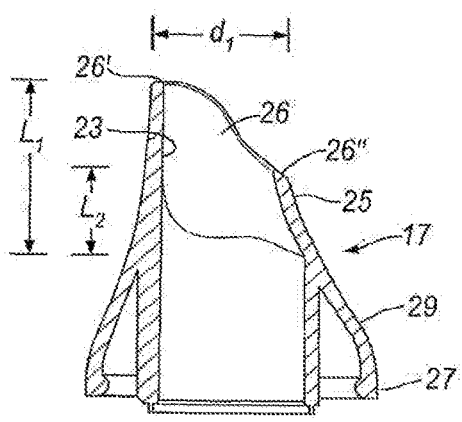
Figure 10C:
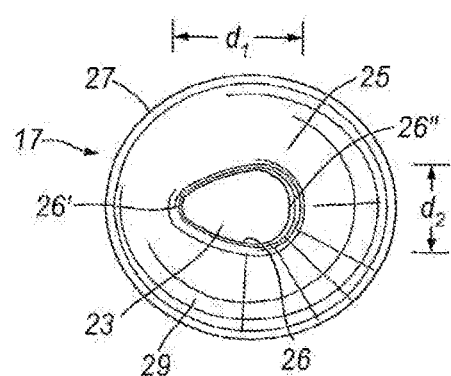

FIGS. 10(a) to (c) illustrate a yet still further modified nosepiece 17 for the delivery device of the above-described embodiment.

In this embodiment the proximal section of the tip element 25 has a wider lateral section than the tip element 25 of the above-described embodiment. With this configuration, the shoulder 29 acts further to promote sealing with the nares of the nostril of the subject.

Figure 11A:
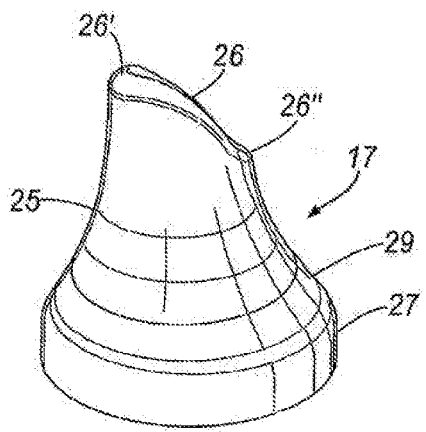
Figure 11B:
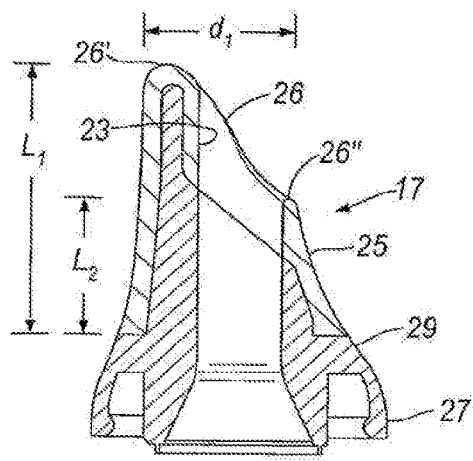
Figure 11C:
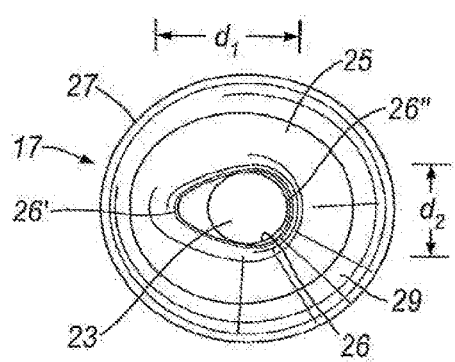

FIGS. 11(a) to (c) illustrate yet another modified nosepiece 17 for the delivery device of the above-described embodiment.

In this embodiment the nosepiece 17 is formed of two body parts 41, 43, a first, inner body part 41, here formed of a rigid material, such as a rigid plastics material, and a second, outer body part 43 which is disposed about the distal end of the inner body part 41 and defines the tip element 25.

In this embodiment the outer body part 43 is formed of a soft, resilient material, such as a rubber or plastics material, which confers sufficient flexibility as to facilitate insertion of the tip element 25 into the nasal valve of the subject, and yet the inner body part 41 confers rigidity in the sagittal plane as to promote expansion of the fleshy tissues at the nasal valve.

Further, in this embodiment the tip element 25 is configured such that the delivery aperture 26 has a symmetric shape, here of circular shape, in a plane orthogonal to the longitudinal axis of the nosepiece 17.

Figure 12A:
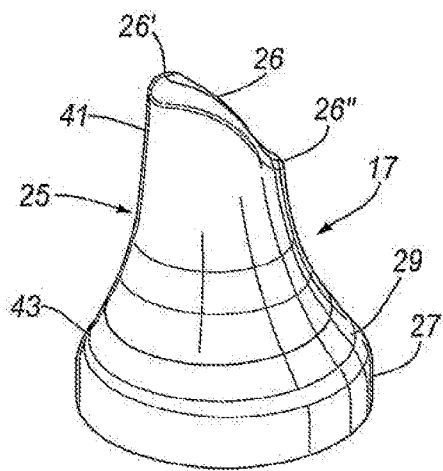
Figure 12B:
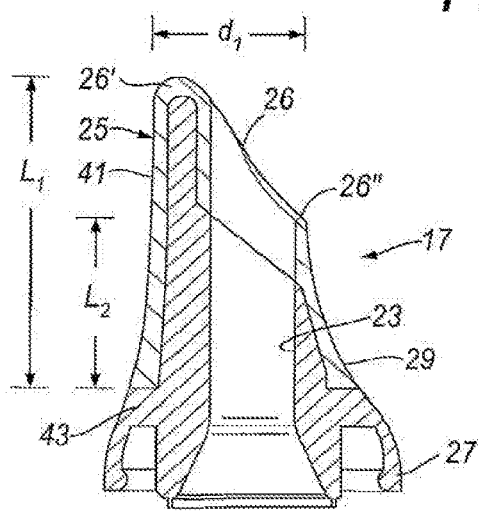
Figure 12C:
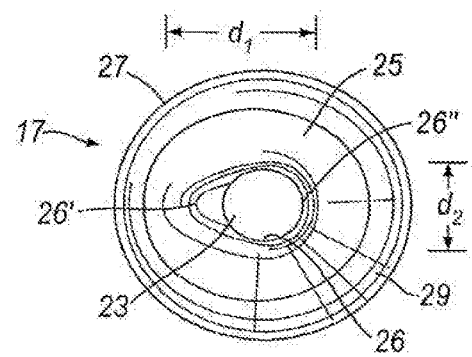
Figure 13A:
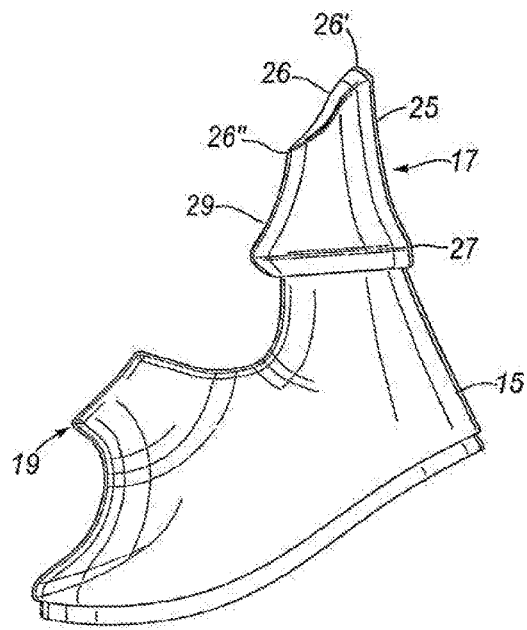
Figure 13B:
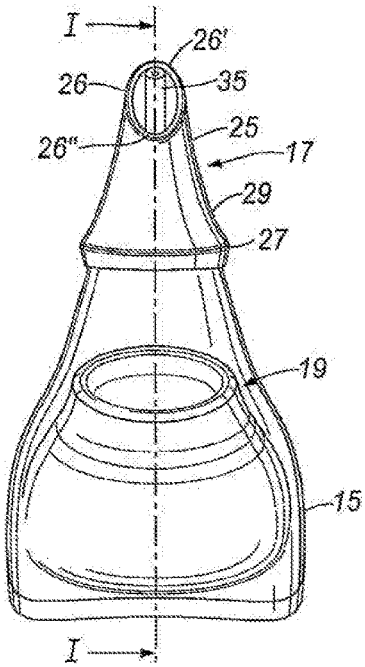
Figure 13C:
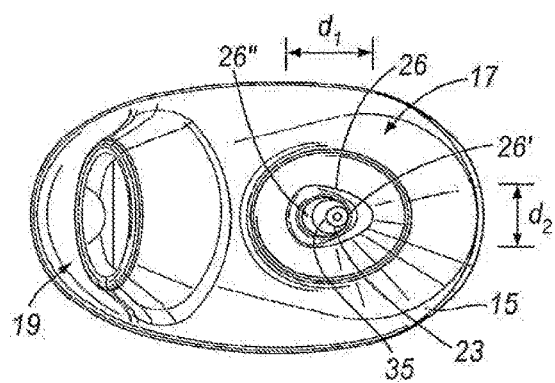
Figure 13D:
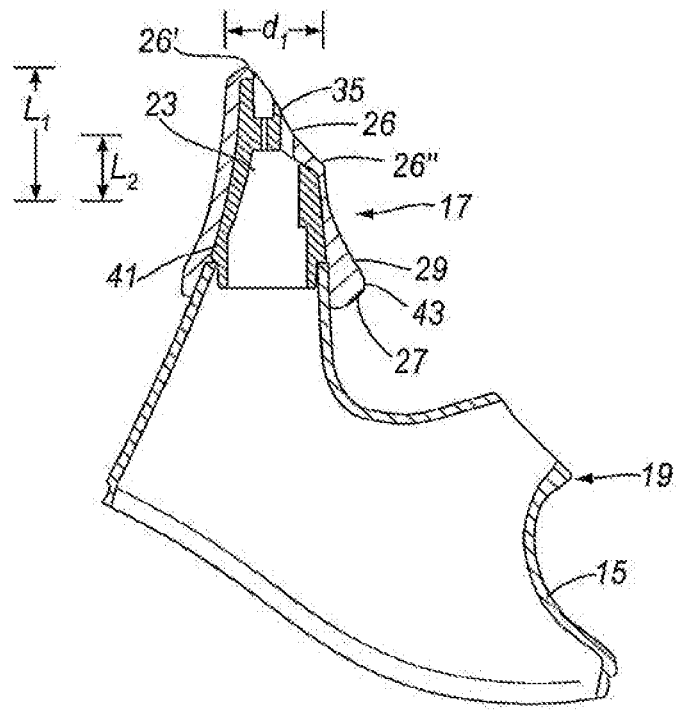

FIGS. 12(a) to (c) illustrate still another modified nosepiece 17 for the delivery device of the above-described embodiment.

In this embodiment the tip element 25 has a greater length than the tip element 25 of the embodiment of FIGS. 11(a) to (c).

Still further, in this embodiment the length l1 of the forwardmost sagittal section 26' is less than twice the length l2 of the rearwardmost sagittal section 26".

FIGS. 13(a) to (d) illustrate still another modified nosepiece 17 for the delivery device of the above-described embodiment.

This embodiment is a modification of the embodiment of FIGS. 11(a) to (c). In this embodiment the nozzle 35 is integrally formed with the tip element 25, here the inner body part 41 of the tip element 25.

FIG. 14 illustrates yet still another modified nosepiece 17 for the delivery device of the above-described embodiment.

This embodiment is a modification of the embodiment of FIGS. 13(a) to (d). In this embodiment the nozzle 35 is integrally formed with the tip element 25, but here the outer body part 43 of the tip element 25.

FIGS. 15 and 16 illustrate a nasal delivery device in accordance with a second embodiment of the present invention.

The delivery device comprises a housing 115, a nosepiece 117 for fitting in a nasal cavity of a subject, and a mouthpiece 119 through which the subject exhales to actuate the delivery device.

The nosepiece 117 is attached to the housing 115 and defines a delivery channel which is in fluid communication with the mouthpiece 119 such that an air flow is delivered into and through the nasal airway of the subject on exhalation by the subject through the mouthpiece 119.

The delivery device further comprises a substance supply unit (not illustrated) for delivering metered doses of a substance from the nosepiece 117, in this embodiment as an aerosol spray.

In this embodiment the substance supply unit is a multi-dose unit for delivering a plurality of metered doses of substance. In another embodiment the substance supply unit could be a single-dose unit for delivering a single metered dose of substance.

The substance supply unit is pre-primeable, in this embodiment by loading a resilient element, and includes a breath-actuated release mechanism which, when triggered, releases the resilient element and actuates the substance supply unit to deliver a metered dose of substance through the nosepiece 117.

The delivery device further comprises a nose gripping member 151, which receives a finger of the subject, in this embodiment the index finger, and is configured to be brought into contact with the skin of the nare of the nostril into which the nosepiece 117 is inserted, such as to allow the skin of the nare of the nostril to be drawn down over the nosepiece 117 and promote the fitting and sealing of the nosepiece 117 in the nasal cavity of the subject and also straighten the flow path and improve access beyond the nasal valve. FIG. 16 illustrates the operation of the nose gripping member 151.

In this embodiment the nose gripping member 151 comprises an attachment element 152 which is attached to the housing 115, and a gripping element 155 which includes a pocket 157 which receives a finger of the subject and is configured to allow for pressing into engagement with the skin of the nare of the nostril.

In this embodiment the attachment element 152 is adhered to the housing 115, here by adhesive tape.

In this embodiment the gripping element 155 comprises a flexible element. In one embodiment the gripping element 155 is formed of a fabric material. In another embodiment the gripping element 155 is formed of a plastics material. In a further embodiment the gripping element 155 is formed of a resilient material, such as a rubber material.

FIGS. 17 and 18 illustrate a nasal delivery device in accordance with a third embodiment of the present invention.

The delivery device comprises a housing 215, a nosepiece 217 for fitting in a nasal cavity of a subject, and a mouthpiece 219 through which the subject exhales to actuate the delivery device.

The nosepiece 217 is attached to the housing 215 and defines a delivery channel which is in fluid communication with the mouthpiece 219 such that an air flow is delivered into and through the nasal airway of the subject on exhalation by the subject through the mouthpiece 219.

The delivery device further comprises a substance supply unit (not illustrated) for delivering metered doses of a substance from the nosepiece 217, in this embodiment as an aerosol spray.

In this embodiment the substance supply unit is a multi-dose unit for delivering a plurality of metered doses of substance. In another embodiment the substance supply unit could be a single-dose unit for delivering a single metered dose of substance.

The substance supply unit is pre-primeable, in this embodiment by loading a resilient element, and includes a breath-actuated release mechanism which, when triggered, releases the resilient element and actuates the substance supply unit to deliver a metered dose of substance through the nosepiece 217.

The delivery device further comprises a nose gripping member 251, which receives a finger of the subject, in this embodiment the index finger, and is configured to be brought into contact with the skin of the nare of the nostril into which the nosepiece 217 is inserted, such as to allow the skin of the nare of the nostril to be drawn down over the nosepiece 217 and promote the fitting and sealing of the nosepiece 217 in the nasal cavity of the subject. FIG. 18 illustrates the operation of the nose gripping member 251.

In this embodiment the nose gripping member 251 comprises a support element 253 which is attached to the housing 215, here pivotally coupled to the housing 215, a biasing element 254, here a spring element, which is operative to bias the support element 253 to an inoperative or rest position, and a gripping element 255 which is attached to the support element 253 and includes a pocket 257 which receives a finger of the subject to allow for pressing into engagement with the skin of the nare of the nostril.

In this embodiment the support element 253 is coupled to the housing 215, such as to allow both for longitudinal and lateral pivoting of the support element 253 against the bias of the biasing element 254.

In this embodiment the gripping element 255 is slideably disposed to the support element 253, such as to allow the gripping element 255 to be drawn downwardly by a retracting action of the finger.

In one embodiment the gripping element 255 is formed of a fabric material. In another embodiment the gripping element 255 is formed of a plastics material. In a further embodiment the gripping element 255 is formed of a resilient material, such as a rubber material.

In one embodiment the gripping element 255 can include a gripping surface which has chemical or mechanical properties for enhancing the grip with the skin of the nose, such as provided by an adhesive material, for example, by an adhesive film or tape or by the application of a glue, liquid, gel, resin or powder, or a vacuum. In one embodiment the gripping element 255 can be impregnated with such an adhesive material, which can allow for prolonged use of the device.

FIGS. 19 and 20 illustrate a nasal delivery device in accordance with a fourth embodiment of the present invention.

The delivery device comprises a housing 315, a nosepiece 317 for fitting in a nasal cavity of a subject, and a mouthpiece 319 through which the subject exhales to actuate the delivery device.

The nosepiece 317 is attached to the housing 315 and defines a delivery channel which is in fluid communication with the mouthpiece 319 such that an air flow is delivered into and through the nasal airway of the subject on exhalation by the subject through the mouthpiece 319.

The delivery device further comprises a substance supply unit (not illustrated) for delivering metered doses of a substance from the nosepiece 317, in this embodiment as an aerosol spray.

In this embodiment the substance supply unit is a multi-dose unit for delivering a plurality of metered doses of substance. In another embodiment the substance supply unit could be a single-dose unit for delivering a single metered dose of substance.

The substance supply unit is pre-primeable, in this embodiment by loading a resilient element, and includes a breath-actuated release mechanism which, when triggered, releases the resilient element and actuates the substance supply unit to deliver a metered dose of substance through the nosepiece 317.

The delivery device further comprises a nose gripping member 351, which receives a finger of the subject, in this embodiment the index finger, and is configured to be brought into contact with the skin of the nare of the nostril into which the nosepiece 317 is inserted, such as to allow the skin of the nare of the nostril to be drawn down over the nosepiece 317 and promote the fitting and sealing of the nosepiece 317 in the nasal cavity of the subject and also straighten the flow path and improve access beyond the nasal valve. FIG. 20 illustrates the operation of the nose gripping member 351.

In this embodiment the nose gripping member 351 comprises an attachment element 352 which is attached to the housing 315, a support element 353 which is coupled, here resiliently coupled to the attachment element 352, and a gripping element 355 which is attached to the support element 353 and is configured to receive a finger of the subject to allow for pressing into engagement with the skin of the nare of the nostril.

In this embodiment the support element 353 is formed of a material which has sufficient resilience as to allow the gripping element 355 normally to maintain an inoperative or rest position and yet be biased, here by resilient deflection of the support element 353, into engagement with the skin of the nare of the nostril.

In this embodiment the support element 353 comprises an elongate support section 357, here of circular section, and the gripping element 355 includes a longitudinal bore 359, here of circular shape, which receives the support section 357, such as to allow both for longitudinal sliding of the gripping element 355 along the support section 357 and lateral rotation about the support section 357.

In this embodiment the nose gripping member 351 further comprises a biasing element 361, here a resilient element, which is disposed to the support element 353 such as to bias the gripping element 355 in a downward direction relative to the nosepiece 317 and thereby facilitate the desired downward pulling action on the skin of the nare of the nostril as achieved by the retracting action of the finger and also straighten the flow path and improve access beyond the nasal valve.

In one embodiment the gripping element 355 is formed of a fabric material. In another embodiment the gripping element 355 is formed of a plastics material. In a further embodiment the gripping element 355 is formed of a resilient material, such as a rubber material.

FIGS. 21 and 22 illustrate a nasal delivery device in accordance with a fifth embodiment of the present invention.

The delivery device comprises a housing 415, a nosepiece 417 for fitting in a nasal cavity of a subject, and a mouthpiece 419 through which the subject exhales to actuate the delivery device.

The nosepiece 417 is attached to the housing 415 and defines a delivery channel which is in fluid communication with the mouthpiece 419 such that an air flow is delivered into and through the nasal airway of the subject on exhalation by the subject through the mouthpiece 419.

The delivery device further comprises a substance supply unit (not illustrated) for delivering metered doses of a substance from the nosepiece 417, in this embodiment as an aerosol spray.

In this embodiment the substance supply unit is a multi-dose unit for delivering a plurality of metered doses of substance. In another embodiment the substance supply unit could be a single-dose unit for delivering a single metered dose of substance.

The substance supply unit is pre-primeable, in this embodiment by loading a resilient element, and includes a breath-actuated release mechanism which, when triggered, releases the resilient element and actuates the substance supply unit to deliver a metered dose of substance through the nosepiece 417.

The delivery device further comprises a nose gripping member 451, which receives a finger of the subject, in this embodiment the index finger, and is configured to be brought into contact with the skin of the nare of the nostril into which the nosepiece 417 is inserted and provide for enhanced grip therewith, such as to allow the skin of the nare of the nostril to be drawn down over the nosepiece 417 and promote the fitting and sealing of the nosepiece 417 in the nasal cavity of the subject and also straighten the flow path and improve access beyond the nasal valve. FIG. 22 illustrates the operation of the nose gripping member 451.

In this embodiment the nose gripping member 451 comprises a gripping element 455, here in the form of a finger-receiving element, typically in the form of a thimble, and an attachment element 452, here a flexible line, which is attached to the gripping element 455 and the housing 415, such as to prevent the gripping element 455 from becoming separated from the housing 415.

In this embodiment the gripping element 455 is configured to allow for attachment to one of the nosepiece 417, the mouthpiece 419 or an actuator element. This configuration advantageously allows for the protection of such components when the device is not in use.

In an alternative embodiment the nose gripping member 451 could comprise only the gripping element 455, and be provided as a separate component. In one embodiment the delivery device could be provided with a plurality of nose gripping members 451.

In one embodiment the gripping element 455 is formed of a fabric material. In another embodiment the gripping element 455 is formed of a plastics material. In a further embodiment the gripping element 455 is formed of a resilient material, such as a rubber material.

FIGS. 23 and 24 illustrate a nasal delivery device in accordance with a sixth embodiment of the present invention.

The delivery device comprises a housing 515, a nosepiece 517 for fitting in a nasal cavity of a subject, and a mouthpiece 519 through which the subject exhales to actuate the delivery device.

The nosepiece 517 is attached to the housing 515 and defines a delivery channel which is in fluid communication with the mouthpiece 519 such that an air flow is delivered into and through the nasal airway of the subject on exhalation by the subject through the mouthpiece 519.

The delivery device further comprises a substance supply unit (not illustrated) for delivering metered doses of a substance from the nosepiece 517, in this embodiment as an aerosol spray.

In this embodiment the substance supply unit is a multi-dose unit for delivering a plurality of metered doses of substance. In another embodiment the substance supply unit could be a single-dose unit for delivering a single metered dose of substance.

The substance supply unit is pre-primeable, in this embodiment by loading a resilient element, and includes a breath-actuated release mechanism which, when triggered, releases the resilient element and actuates the substance supply unit to deliver a metered dose of substance through the nosepiece 517.

The delivery device further comprises a nose gripping member 551, in this embodiment as a member separate to the housing 515 of the delivery device, which is configured to receive a finger of the subject, in this embodiment the index finger, such as to allow the skin of the nare of the nostril to be drawn down over the nosepiece 517 and promote the fitting and sealing of the nosepiece 517 in the nasal cavity of the subject and also straighten the flow path and improve access beyond the nasal valve. FIG. 24 illustrates the operation of the nose gripping member 551.

In this embodiment the nose gripping member 551 comprises a gripping element 555, which is fixed to the nose of the subject, such as to allow for gripping by the finger of the subject.

In this embodiment the nose gripping member 551 further comprises an attachment element 552, here a resilient element, which acts to fasten the gripping element 555 to the nose.

In an alternative embodiment the attachment element 552 could be in the form of a frame which fits to the face of the subject, for example, in the manner of spectacles.

In an alternative embodiment the gripping element 555 could be adhered to the nose, for example, by adhesive tape.

In one embodiment the gripping element 555 could take the form of a nasal dilator which is fixed to the nose.

Finally, it will be understood that the present invention has been described in its preferred embodiments and can be modified in many different ways without departing from the scope of the invention as defined by the appended claims.

FIGS. 25(*a*) and (*b*) illustrate a further modification of the nosepiece 17 of the delivery device of FIG. 2.

In this embodiment the tip element 25 comprises a flexible nosepiece member 51 and an expansion member 53 which acts to expand the flexible nosepiece member 51 laterally on the application of an insertion force F substantially along the longitudinal axis of the nosepiece 17, as illustrated in FIG. 25(*b*).

In this embodiment the expansion member 53 comprises a plurality of elongate elements 55 which are disposed within the flexible nosepiece member 51 such as normally to have a first, flat configuration in which the flexible nosepiece member 51 has a contracted state, as illustrated in FIG. 25(*a*), and, on the application of an insertion force F substantially along the longitudinal axis of the nosepiece 17, at least one of the elongate elements 55' is longitudinally displaced relative to the at least one other elongate element 55", such as to expand the flexible nosepiece member 51 into an expanded state, as illustrated in FIG. 25(*b*).

FIGS. 26(*a*) and (*b*) illustrate a yet further modification of the nosepiece of the delivery device of FIG. 2.

In this embodiment the tip element 25 comprises a flexible nosepiece member 61 and an expansion member 63 which acts to expand the flexible nosepiece member 61 laterally on the application of an insertion force F substantially along the longitudinal axis of the nosepiece 17, as illustrated in FIG. 26(*b*).

In this embodiment the expansion member 63 comprises a coil which is disposed within the flexible nosepiece member 61 such as normally to have a first, flat configuration in which the flexible nosepiece member 61 has a contracted state, as illustrated in FIG. 26(*a*), and, on the application of an insertion force F substantially along the longitudinal axis of the nosepiece 17, the coil is longitudinally compressed, such as to expand the coil and configure the flexible nosepiece member 61 in an expanded state, as illustrated in FIG. 26(*b*).

FIGS. 27(*a*) and (*b*) illustrate a still yet further modification of the nosepiece of the delivery device of FIG. 2.

In this embodiment the tip element 25 comprises a flexible nosepiece member 71 which is inflatable from a first configuration, as illustrated in FIG. 27(*a*), in which the delivery aperture 26 is in a closed configuration, here substantially closed, to an open configuration, as illustrated in FIG. 27(*b*), in which the delivery aperture 26 is open, such as to allow for the delivery of substance therethrough.

In this embodiment the flexible nosepiece member 71 includes an annular chamber 73 which surrounds the delivery channel 23 at the delivery aperture 26, which is normally in a collapsed, uninflated state, and, on inflation, acts to define a relatively-rigid annulus which holds open the delivery aperture 26.

In one embodiment the inflation chamber 73 can be inflated by a gas, such as from the exhalation breath of a subject or by mechanical operation by a subject, either directly, such as by the application of a manual force with the fingers of the subject, or through an actuator, such as a spring. In an alternative embodiment the inflation chamber 73 can be inflated by a liquid.

The invention claimed is:

1. A method of fitting a nasal delivery device to a nostril of a subject, the method comprising:
    inserting a nosepiece of the nasal delivery device into one of the nostrils of the subject, with the nasal delivery device having a first alignment;
    twisting the nosepiece in the nostril so as to rotate the nasal delivery device to have a second alignment which is different from the first alignment and in which a mouthpiece of the nasal delivery device is aligned with a mouth of the subject;
    sealing a nare of the nostril against the nosepiece; and
    causing the subject to exhale through the mouthpiece.

2. The method of claim 1, further comprising:
    applying a grip-enhancing agent to an exterior surface of a nose of the subject.

3. The method of claim 1, wherein the nosepiece comprises a tip element.

4. The method of claim 3, wherein the tip element is substantially elliptical.

5. The method of claim 3, wherein the tip element is substantially rectangular.

6. The method of claim 3, wherein the tip element comprises a delivery aperture.

7. The method of claim 3, wherein the tip element is tapered.

8. The method of claim 1, wherein the nasal delivery device comprises a substance supply unit and a nose gripping member.

9. The method of claim 8, wherein the nose gripping member is tethered to a body of the nasal delivery device.

10. The method of claim 8, wherein the nose gripping member comprises a gripping element which is configured to be fixed to a nose of the subject.

11. The method of claim 1, further comprising;
    pressing a finger against the skin of the nose so as to press the nare of the nostril against the nosepiece.

12. The method of claim 1, further comprising:
    pulling the nare of the nostril over the nosepiece.

13. The method of claim 12, wherein the pulling is done by a finger.

* * * * *